US006919346B2

(12) United States Patent
Clark et al.

(10) Patent No.: US 6,919,346 B2
(45) Date of Patent: Jul. 19, 2005

(54) ISOXAZOLONE COMPOUNDS USEFUL IN TREATING DISEASES ASSOCIATED WITH UNWANTED CYTOKINE ACTIVITY

(75) Inventors: Michael Philip Clark, Loveland, OH (US); Jane Far-Jine Djung, Mason, OH (US); Steven Karl Laughlin, Taylor Mill, KY (US); Joshua Spector Tullis, Broomfield, CO (US); Michael George Natchus, Alpharetta, GA (US); Biswanath De, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1 day.

(21) Appl. No.: 10/726,111

(22) Filed: Dec. 2, 2003

(65) Prior Publication Data

US 2004/0122025 A1 Jun. 24, 2004

Related U.S. Application Data

(62) Division of application No. 10/140,541, filed on May 7, 2002, now Pat. No. 6,790,846.
(60) Provisional application No. 60/293,889, filed on May 24, 2001.

(51) Int. Cl.$^7$ .................... C07D 413/04; A61K 31/506; A61P 9/04; A61P 19/02

(52) U.S. Cl. ...................... 514/256; 514/269; 544/315; 544/317

(58) Field of Search ............................... 544/315, 317; 514/256, 269

(56) References Cited

U.S. PATENT DOCUMENTS

| 5,686,455 A | 11/1997 | Adams et al. |
| 5,776,954 A | 7/1998 | De Laszlo et al. |

FOREIGN PATENT DOCUMENTS

| WO | WO 95/13067 A1 | 5/1995 |
| WO | WO 97/47618 A1 | 12/1997 |
| WO | WO 99/03837 A1 | 1/1999 |
| WO | WO 00/10563 A1 | 3/2000 |
| WO | WO 00/26209 A1 | 5/2000 |
| WO | WO 01/12621 A1 | 2/2001 |

OTHER PUBLICATIONS

Dinarello, C. A., "Interleukin–1", *Reviews of Infectious Diseases*, vol. 6, No. 1, pp. 51–95, 1984.
Maini, R. et al., "Infliximab (chimeric anti–tumour necrosis factor α monoclonal antibody) versus placebo in rheumatoid arthritis patients receiving concomitant methotrexate: a randomised phase III trial", *The Lancet*, vol. 354, pp. 1932–1939, 1999.

Weinblatt, M. E. et al., "A Trial of Etanercept, a Recombinant Tumor Necrosis Factor Receptors:Fc Fusion Protein, in Patients with Rheumatoid Arthritis Receiving Methotrexate", *The New England J. of Medicine*, vol. 340, No. 4, pp. 253–259, 1999.
Pelletier, J.P., et al., "coordinate Synthesis of Stromelysin, Interleukin–1, and Oncogene Proteins in Experimental Osteoarthritis", *Amer. J. of Pathology*, vol. 142, No. 1, pp. 95–105, 1993.
Farahat, M.N. et al., "Cytokine Expression in Synovial Membranes of Patients with Rheumatoid Arthritis and Osteoarthritis", *Annals of the Rheumatic Diseases*, vol. 52, pp. 870–875, 1993.
Tiku, K. et al., "Articular Chondrocytes Secrete IL–1, Express Membrane IL–1, and Have IL–1 Inhibitory Activity", *Cellular Immunology*, Vo.. 140, pp. 1–20, 1992.
Web, G. R., et al., "Chondrocyte tumor necrosis factor receptors and focal loss of cartilage in osteoarthritis", *Osteoarthritis and Cartilage*, vol. 5, pp. 427–437, 1997.
Westacott, A. F., et al., "Tumor necrosis factor alpha can contribute to focal loss of cartilage in osteoarthritis", *Osteoarthritis and Cartilage*, vol. 8, pp. 213–221, 2000.
McDaniel, M.L., et al., "Cytokines and Nitric Oxide in Islet Inflammation and Diabetes", *Proc. Soc. Exp. Biol. Med*, vol. 211, No. 1, pp. 24–32, 1996.
Rankin, E.C.C., et al., "The Therapeutic Effects of an Engineered Human Anti–Tumor Necrosis Factor Necrosis Factor alpha Antibody (CDP571) in Rheumatoid Arthritis" *British J. of Rheumatology*, vol. 34, pp. 334–342, 1995.
Stack, W.A., et al., "Randomised controlled trial of CDP571 antibody to tumour necrosis factor–α in Crohn's disease", *The Lancet*, vol. 249, No. 9051, pp. 521–524, 1997.
Han, J., et al., "Regulation of MEF2 by p38 MAPK and Its Implication in Cardiomyocyte Biology", *Trends Cardiovasc Med.*, vol. 10, No. 1, pp. 19–22, 2000.

(Continued)

*Primary Examiner*—Venkataraman Balasubramanian
(74) *Attorney, Agent, or Firm*—Richard S. Echler, Sr.

(57) ABSTRACT

Isoxazolone compounds having the generic structure:

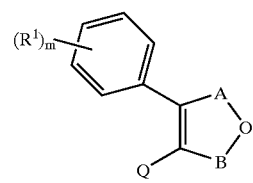

are used to treat disease associated with unwanted cytokine activity, including rheumatoid arthritis, osteoarthritis, diabetes, HIV/AIDS, inflammatory bowel disease, Crohn's disease, ulcerative colitis, congestive heart, hypertension, chronic obstructive pulmonary disease, septic shock syndrome, tuberculosis, adult respiratory distress, asthma, atherosclerosis, muscle degeneration, periodontal disease, cachexia, Reiter's syndrome, gout, acute synovitis, anorexia and bulimia nervosa fever, malaise, myalgia and headaches.

11 Claims, No Drawings

OTHER PUBLICATIONS

Hunter, J.J., et al., "Signaling Pathways for Cardiac Hypertrophy and Failure", *The New England J. of Medicine*, vol. 341, No. 17, pp. 1276–1283, 1999.

Behr, T.M., et al., "Sustained Activation of Cardiac P38 Mitogen Activated Protein Kinase in the Development of Heart Failure: Premature Mortality is Abolished by Chronic P38 Inhibition in Rat Model of Cardiac Hypertrophy and Failure", *Basic Science*, vol. 102, pp. 289, 2000.

Shimamoto, A., et al., "Inhibition of P38 Mitogen–Activated Protein Kinase Suppresses Interleukin–1β–Expression and Prevents Progression of Cardiac Hypertrophy and Congestive Heart Failure in Rats", *Basic Science*, vol. 102, pp. 289, 2000.

Aukrust, P., et al., "Cytokine Network in Congestive Heart Failure Secondary to Ischemic or Idiopathic Dilated Cardiomyopathy", *Am. J. Cardiol*, vol. 83, No. 3, pp. 376–382, 1999.

Singh, A., et al., "Inducible Nitric Oxide Synthase in Vascular Smooth muscle Cells From Prehypertensive Spontaneously Hypertensive Rats", *Am. J. Hypertens.*, vol. 9, No. 9, pp. 867–877, 1996.

Dinarello, C.A., "Interleukin–1 and Interleukin–1 Receptor Antagonist", *Supplement to Nutrition*, vol. 11, No. 5, pp. 492–494, 1995.

Rrenzetti, L.M., "Ro 45–2081, a TNF receptor fusion protein, prevents inflammatory responses in the airways", *Inflammation Research*, 46 Suppl. vol. 2, pp. S143–S144, 1997.

Elhage, R. et al., "Differential Effects of Interleukin–1 Receptor antagonist and Tumor Necrosis Factor Binding Protein on Fatty–Streak Formation in apolipoprotein E–Deficient Mice", *Circulation*, vol. 97, No. 3, pp. 242–244, 1998.

Howells, G.L., "Cytokine networks in destructive periodontal disease", *Oral Diseases*, vol. 1, pp. 266–270, 1995.

Holden, R.J. et al., "The Role of tumor Necrosis Factor–α in the Pathogenesis of anorexia and Bulimia Nervosa, Cancer Cachexia and Obesity", *Medical Hypotheses*, vol. 47, pp. 423–438, 1996.

Beisel, W.R., "Herman Award Lecture, 1995: Infection–induced mainutrition–from cholera to cytokines", *Am. J. Clin. Nutr.*, vol. 62, pp. 813–819, 1995.

Salituro, F.G. et al., "Inhibitors of p38 MAP Kinase: Therapeutic Intervention in Cytokine–Mediated Diseases", *Current Medicinal Chemistry*, vol. 6, pp. 807–823, 1999.

Foster, M.L. et al., "Potential of p38 Inhibitors in the Treatment of Rheumatoid Arthritis", *Drug News Perspect*, vol. 13, No. 8, pp. 488–497, 2000.

Adams, J.L. et al., "Pyrimidinylimidazole Inhibitors of CSBP/P38 Kinase Demonstrating Decreased Inhibition of Hepatic Cytochrome P450 Enzymes", *Bioorganic & Medicinal chemistry Letters*, vol. 8, pp. 3111–3116, 1998.

ISOXAZOLONE COMPOUNDS USEFUL IN TREATING DISEASES ASSOCIATED WITH UNWANTED CYTOKINE ACTIVITY

CROSS REFERENCE TO RELATED APPLICATIONS

This application is a Divisional Application of application Ser. No. 10/140,541, filed May 7, 2002, now U.S. Pat. No. 6,790,846, which claims priority under Title 35, United States Code 119(e) from Provisional Application Ser. No. 60/293,889, filed May 24, 2001.

TECHNICAL FIELD

The present invention is directed to certain isoxazolone compounds that inhibit the release of inflammatory cytokines such as interleukin-1 (IL-1) and tumor necrosis factor (TNF) from cells. The compounds of the invention, therefore, are useful in treating diseases involving unwanted cytokine activity.

BACKGROUND

Many cytokine-mediated diseases and conditions are associated with excessive or unregulated production or activity of one or more cytokines such as interleukin 1 (IL-1), tumor necrosis factor (TNF), interleukin 6 (IL-6) and interleukin 8 (IL-8). IL-1 and TNF are important proinflammatory cytokines, which along with several other related molecules, mediate inflammatory cellular response in a wide variety of diseases and conditions. Proinflammatory cytokines such as IL-1 and TNF stimulate other inflammatory mediators such as nitric oxide, cyclooxygenase-2, matrix metalloproteinases. The inhibition of these cytokines is consequently both directly and indirectly beneficial in controlling, reducing and alleviating many of these disease states.

Elevated levels of proinflammatory cytokines are implicated in many disease states, including rheumatoid arthritis (Dinarello, C. A., et al. 1984, *Rev. Infect. Disease* 6:51; Maini, R. E. 1999, *The Lancet* 354:1932; Weinblatt, M. E. 1999, *New Eng. J. Med.* 340:253), osteoarthritis (Pelletier and Pelletier 1989, *J. Rheum.* 16:19; Pelletier, et al. 1993, *Am. J. Path.* 142:95; Farahat, et al. 1993, *Ann. Rheum. Dis.* 52:870; Tiku, et al. 1992, *Cell Immunol.* 140:1; Webb, et al. 1997, *O. & C.* 5:427; Westacott, et al. 2000, *O. & C.* 8:213), diabetes (McDaniel, et al. 1996, *Proc. Soc. Exp. Biol. Med.* 211:24), HIV/AIDS (Kreuzer, et al. 1997, *Clin. Exp. Immunol.* 45:559), acute and chronic inflammatory diseases, such as the inflammatory reaction induced by endotoxin or inflammatory bowel disease, Crohn's disease and ulcerative colitis (Rankin, E. C. C., et al. 1997, *British J. Rheum.* 35:334; Stack, W. A., et al. 1997, *The Lancet* 349:521); congestive heart failure Han et al. 2000, *Trends Cardiovasc. Med.* 10:19; Hunter et al. 1999, *N. Engl. J. Med.* 341:1276; Behr et al. 2000, *Circ.* 102:II-289; Shimamoto et al. 2000, *Circ:*102:II-289; Aukrust et al. 1999, *Am. J. Cardiol.* 83:376, hypertension (Singh, et al. 1996 *J. Hypertension* 9:867), chronic obstructive pulmonary disease, septic shock syndrome (Dinarello, C. A. 1995, *Nutrition* 11:492), tuberculosis, adult respiratory distress, asthma (Renzetti, et al. *Inflammation Res.* 46:S143), atherosclerosis (Elhage, et al. 1998, *Circulation* 97:242), muscle degeneration, periodontal disease (Howells 1995, *Oral Dis.* 1:266), cachexia, Reiter's syndrome, gout, acute synovitis, eating disorders including anorexia and bulimia nervosa (Holden, et al. 1996, *Med. Hypothesis* 47:423), fever, malaise, myalgia and headaches (Beisel 1995 *Am. J. Clin. Nutr.* 62:813). Inhibition of proinflammatory cytokine production, therefore, may offer the opportunity to treat or prevent a wide range of diseases and conditions involving elevated levels of proinflammatory cytokines.

Numerous small molecule inhibitors of cytokine production have been disclosed. (See Salituro, F. G. et al. 1999, 6, 807–823 and references cited therein). In particular, 1,2,4-triazoles (WO 00/10563 and WO 97/47618), isoxazoles (WO 01/12621), and imidazoles (WO 00/26209, WO 99/03837 and references therein) have been disclosed. However, certain liver toxicities, such as increased liver size and increased cytochrome P450 induction, have recently been reported (Foster, M. L. et al., *Drug News Perspect*, 2000, 13(8), 488–497 and Adams, J. L. et al., *Bioorg Med Chem Lett*, 1998, 8, 3111–3116). In light of the this potential toxicity and the risks associated with developing human drugs, a continuing need exists for potent new small molecule inhibitors of cytokine production with improved pharmacokinetic and safety profiles.

All documents cited are, in relevant part, incorporated herein by reference; the citation of any document is not to be construed as an admission that it is prior art with respect to the present invention.

SUMMARY OF THE INVENTION

The invention provides compounds which are potent cytokine inhibitors and which are effective in treating conditions characterized by excess activity of these enzymes. In particular, the present invention is directed to compounds having a structure according to Formula (I):

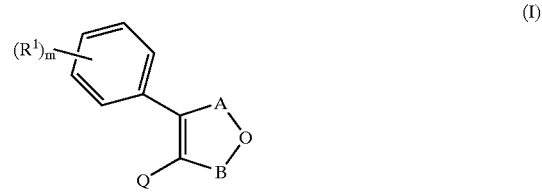

wherein $R^1$, m, A, B, and Q are defined herein.

The invention also includes optical isomers, diastereomers, and enantiomers of the structure above, and pharmaceutically-acceptable salts thereof.

The compounds of the present invention are useful for the treatment of diseases and conditions which are characterized by unwanted cytokine activity. Accordingly, the invention further provides pharmaceutical compositions comprising these compounds. The invention still further provides methods of treatment for diseases associated with unwanted cytokine activity using these compounds or the compositions comprising them.

DETAILED DESCRIPTION OF THE INVENTION

The invention is directed to a novel group of compounds which are potent inhibitors of cytokines and which are effective in treating conditions characterized by excess activity of these enzymes.

Terms and Definitions

"Alkenyl" is a monovalent hydrocarbon chain having 2 to 18 carbon atoms, preferably 2 to 12, more preferably 2 to 6 carbon atoms and at least one (preferably only one) carbon-carbon double bond. Alkenyl groups may be straight or branched. Preferred branched alkenyl groups have one or two branches, preferably one branch. Alkenyl groups may be unsubstituted or substituted with from 1 to 4 substituents. Preferred substituted alkenyl groups have 1 to 3 substituents unless otherwise specified. Alkenyl group substituents include halo, OH, alkoxy, aryloxy (e.g., phenoxy), aryl (e.g., phenyl), heteroaryl, cycloalkyl, heterocycloalkyl, thioalkoxy, thioaryloxy, amino, keto, thioketo, nitro, and cyano. Preferred alkenyl group substituents include halo, OH, alkoxy, aryloxy (e.g., phenoxy), aryl (e.g., phenyl), heteroaryl, heterocycloalkyl, amino, and keto. The term "lower alkenyl" refers to an alkenyl group having from 2 to 6, preferably from 2 to 4, carbon atoms.

"Alkyl" is a monovalent saturated hydrocarbon chain having 1 to 18 carbon atoms, preferably 1 to 12, more preferably 1 to 6 carbon atoms. Alkyl groups may be straight or branched. Preferred branched alkyl groups have one or two branches, preferably one branch. Alkyl groups may be unsubstituted or substituted with from 1 to 4 substituents. Preferred substituted alkyl groups have 1 to 3 substituents unless otherwise specified. Alkyl group substituents include halo, OH, alkoxy, aryloxy (e.g., phenoxy), aryl (e.g., phenyl), heteroaryl, cycloalkyl, heterocycloalkyl, thioalkoxy, thioaryloxy, amino, keto, thioketo, nitro, and cyano. Preferred alkyl group substituents include halo, OH, alkoxy, aryloxy (e.g., phenoxy), aryl (e.g., phenyl), heteroaryl, heterocycloalkyl, amino, and keto. The term "lower alkyl" refers to an alkyl group having from 1 to 6, preferably from 1 to 4, carbon atoms.

"Alkoxy" refers to the group —OR where R is alkyl, alkenyl, alkynyl, heteroalkyl, heteroalkenyl, heteroalkynyl, cycloalkyl, cycloalkenyl, or heterocycloalkyl. Preferred alkoxy groups include methoxy, ethoxy, and iso-propoxy.

"Alkynyl" is a monovalent hydrocarbon chain having 2 to 18 carbon atoms, preferably 2 to 12, more preferably 2 to 6 carbon atoms and at least one (preferably only one) carbon-carbon triple bond. Alkynyl groups may be straight or branched. Preferred branched alkynyl groups have one or two branches, preferably one branch. Alkynyl groups may be unsubstituted or substituted with from 1 to 4 substituents. Preferred substituted alkynyl groups have 1 to 3 substituents unless otherwise specified. Alkynyl group substituents include halo, OH, alkoxy, aryloxy (e.g., phenoxy), aryl (e.g., phenyl), heteroaryl, cycloalkyl, heterocycloalkyl, thioalkoxy, thioaryloxy, amino, keto, thioketo, nitro, and cyano. Preferred alkynyl group substituents include halo, OH, alkoxy, aryloxy (e.g., phenoxy), aryl (e.g., phenyl), heteroaryl, heterocycloalkyl, amino, and keto. The term "lower alkynyl" refers to an alkynyl group having from 2 to 6, preferably from 2 to 4, carbon atoms.

"Amino" refers to the group —N(R)$_2$ where each R is independently chosen from the group consisting of: hydrogen, alkyl, alkenyl, alkynyl, heteroalkyl, heteroalkenyl, heteroalkynyl, cycloalkyl, cycloalkenyl, heterocycloalkyl, aryl and heteroaryl. Preferred amino groups include NH$_2$, NHCH$_3$, and NHC(O)CH$_3$.

"Aryl" is an aromatic hydrocarbon ring system. Aryl rings are either monocyclic ring systems or fused bicyclic ring systems. Monocyclic aryl rings contain 6 carbon atoms in the ring. Monocyclic aryl rings are also referred to as phenyl rings. Bicyclic aryl rings contain from 8 to 12 carbon atoms, preferably 8 to 10 carbon atoms, more preferably 10 carbon atoms, in the ring. Bicyclic aryl rings include ring systems wherein both rings are aromatic or only one ring is aromatic. Preferred bicyclic aryl rings comprise 5-, 6- or 7-membered rings fused to 5-, 6-, or 7-membered rings. Preferred aryl rings include naphthyl, tolyl, xylyl, and phenyl. The most preferred aryl ring is phenyl. Aryl rings may be unsubstituted or substituted with from 1 to 5, preferably from 1 to 3, more preferably from 1 to 2 substituents on the ring. Preferred aryl rings are unsubstituted or substituted with 1 or 2 substituents. Aryl rings may be substituted with halo, cyano, nitro, hydroxy, amino, alkyl, lower alkenyl, lower alkynyl, heteroalkyl, aryloxy, alkoxy, methylenedioxy [which refers to the group (—OCH$_2$O—)], thioalkoxy, thioaryloxy, or any combination thereof. Preferred aryl ring substituents include halo, cyano, amino, alkyl, heteroalkyl, aryloxy, alkoxy, methylenedioxy, thioalkoxy, thioaryloxy.

"Aryloxy" refers to the group —OR where R is aryl or heteroaryl. Preferred aryloxy groups include phenoxy and pyridinyloxy.

"Cyano" refers to the group —CN.

"Cycloalkyl" is a saturated hydrocarbon ring. Cycloalkyl rings are monocyclic, or are fused, spiro, or bridged bicyclic ring systems. Preferred cycloalkyl rings are monocyclic. Monocyclic cycloalkyl rings contain from 3 to 10 carbon atoms, preferably from 3 to 7 carbon atoms, more preferably 3, 5, or 6 carbon atoms in the ring. Bicyclic cycloalkyl rings contain from 7 to 17 carbon atoms, preferably from 7 to 12 carbon atoms, in the ring. Preferred bicyclic cycloalkyl rings comprise 5-, 6- or 7-membered rings fused to 5-, 6-, or 7-membered rings. Preferred cycloalkyl rings include cyclopropyl, cyclopentyl, and cyclohexyl. Cycloalkyl rings may be unsubstituted or substituted with from 1 to 4 substituents on the ring. Cycloalkyl group substituents include alkyl, aryl (e.g., phenyl), alkoxy, aryloxy (e.g., phenoxy), thioalkoxy, thioaryloxy, heteroaryl, heterocycloalkyl, halo, hydroxy, amino, keto, thioketo, nitro, and cyano. Preferred cycloalkyl group substituents include halo, hydroxy, alkyl, aryl (e.g., phenyl), alkoxy, aryloxy (e.g., phenoxy), heteroaryl, heterocycloalkyl, amino, and keto. More preferred cycloalkyl group substituents include hydroxy, alkyl, and alkoxy.

"Cycloalkenyl" is an unsaturated hydrocarbon ring. Cycloalkenyl rings are not aromatic and contain at least one (preferably only one) carbon-carbon double bond. Cycloalkenyl rings are monocyclic, or are fused, spiro, or bridged bicyclic ring systems. Preferred cycloalkenyl rings are monocyclic. Monocyclic cycloalkenyl rings contain from 5 to 10 carbon atoms, preferably from 5 to 7 carbon atoms, more preferably 5 or 6 carbon atoms in the ring. Bicyclic cycloalkenyl rings contain from 8 to 12 carbon atoms in the ring. Preferred bicyclic cycloalkenyl rings comprise 5-, 6- or 7-membered rings fused to 5-, 6-, or 7-membered rings. Cycloalkenyl rings may be unsubstituted or substituted with from 1 to 4 substituents on the ring. Cycloalkenyl group substituents include alkyl, aryl (e.g., phenyl), alkoxy, aryloxy (e.g., phenoxy), thioalkoxy, thioaryloxy, heteroaryl, heterocycloalkyl, halo, hydroxy, amino, keto, thioketo, nitro, and cyano. Preferred cycloalkenyl group substituents include halo, hydroxy, alkyl, alkoxy, aryloxy (e.g., phenoxy), aryl (e.g., phenyl), heteroaryl, heterocycloalkyl, amino, and keto. More preferred cycloalkyl group substituents include OH, alkyl, alkoxy, and keto.

"Halo" or "halogen" is fluoro, chloro, bromo or iodo. Preferred halo are fluoro, chloro and bromo. More preferred halo are chloro and fluoro, especially fluoro.

"Heteroalkenyl" is a monovalent chain having 3 to 18 member atoms (carbon and heteroatoms) in the chain, preferably 3 to 12, more preferably 3 to 6 member atoms and at least one (preferably only one) carbon-carbon double bond. Heteroalkenyl chains have at least one heteroatom member atom. Heteroalkenyl groups may be straight or branched. Preferred branched heteroalkenyl groups have one or two branches, preferably one branch. Heteroalkenyl groups may be unsubstituted or substituted with from 1 to 4 substituents.

Preferred substituted heteroalkenyl groups have 1 to 3 substituents unless otherwise specified. Heteroalkenyl group substituents include halo, hydroxy, alkyl, alkoxy, aryloxy (e.g., phenoxy), thioalkoxy, thioaryloxy, aryl (e.g., phenyl), heteroaryl, cycloalkyl, heterocycloalkyl, amino, keto, thioketo, nitro, and cyano. Preferred heteroalkenyl group substituents include halo, hydroxy, alkyl, alkoxy, aryloxy (e.g., phenoxy), aryl (e.g., phenyl), heteroaryl, heterocycloalkyl, amino, and keto. The term "lower heteroalkenyl" refers to a heteroalkenyl group having from 3 to 6, preferably from 3 to 4, member atoms.

"Heteroalkyl" is a monovalent saturated chain having from 2 to 18 member atoms (carbon and heteroatoms) in the chain, preferably 2 to 12, more preferably 2 to 6. Heteroalkyl chains have at least one heteroatom member atom. Heteroalkyl groups may be straight or branched. Preferred branched heteroalkyl have one or two branches, preferably one branch. Heteroalkyl chains may be unsubstituted or substituted with from 1 to 4 substituents. Preferred substituted heteroalkyl groups have 1 to 3 substituents unless otherwise specified. Heteroalkyl group substituents include aryl (e.g., phenyl), alkoxy, aryloxy (e.g., phenoxy), thioalkoxy, thioaryloxy, heteroaryl, cycloalkyl, heterocycloalkyl, halo, hydroxy, amino, keto, thioketo, nitro, and cyano. Preferred heteroalkyl group substituents include aryl (e.g., phenyl), alkoxy, aryloxy (e.g., phenoxy), heteroaryl, heterocycloalkyl, halo, hydroxy, amino, and keto. The term "lower heteroalkyl" refers to a heteroalkyl group having from 2 to 6, preferably from 2 to 4, member atoms.

"Heteroalkynyl" is a monovalent chain having 3 to 18 member atoms (carbon and heteroatoms) in the chain, preferably 3 to 12, more preferably 3 to 6 member atoms and at least one (preferably only one) carbon-carbon triple bond. Heteroalkynyl chains have at least one heteroatom member atom. Heteroalkynyl groups may be straight or branched. Preferred branched heteroalkynyl groups have one or two branches, preferably one branch. Heteroalkynyl groups may be unsubstituted or substituted with from 1 to 4 substituents. Preferred substituted heteroalkynyl groups have 1 to 3 substituents unless otherwise specified. Heteroalkynyl group substituents include alkyl, aryl (e.g., phenyl), alkoxy, aryloxy (e.g., phenoxy), heteroaryl, cycloalkyl, heterocycloalkyl, halo, hydroxy, amino, keto, thioketo, nitro, and cyano. Preferred heteroalkynyl group substituents include alkyl, aryl (e.g., phenyl), alkoxy, aryloxy (e.g., phenoxy), heteroaryl, heterocycloalkyl, halo, hydroxy, amino, and keto. The term "lower heteroalkynyl" refers to a heteroalkynyl group having from 3 to 6, preferably from 3 to 4, member atoms.

"Heteroaryl" is an aromatic ring containing carbon atoms and from 1 to 6 heteroatoms in the ring. Heteroaryl rings are monocyclic or fused polycyclic ring systems. Monocyclic heteroaryl rings contain from 5 to 9 member atoms (carbon and heteroatoms), preferably 5 or 6 member atoms, in the ring. Polycyclic heteroaryl rings contain 8 to 17 member atoms, preferably 8 to 12 member atoms, in the ring. Polycyclic heteroaryl rings include ring systems wherein at least one ring is heteroaryl (the second ring may be aryl, heteroaryl, cycloalkyl, cycloalkenyl, or heterocycloalkyl). Preferred bicyclic heteroaryl ring systems comprise 5-, 6- or 7-membered rings fused to 5-, 6-, or 7-membered rings. Preferred heteroaryl rings include, but are not limited to, the following rings:

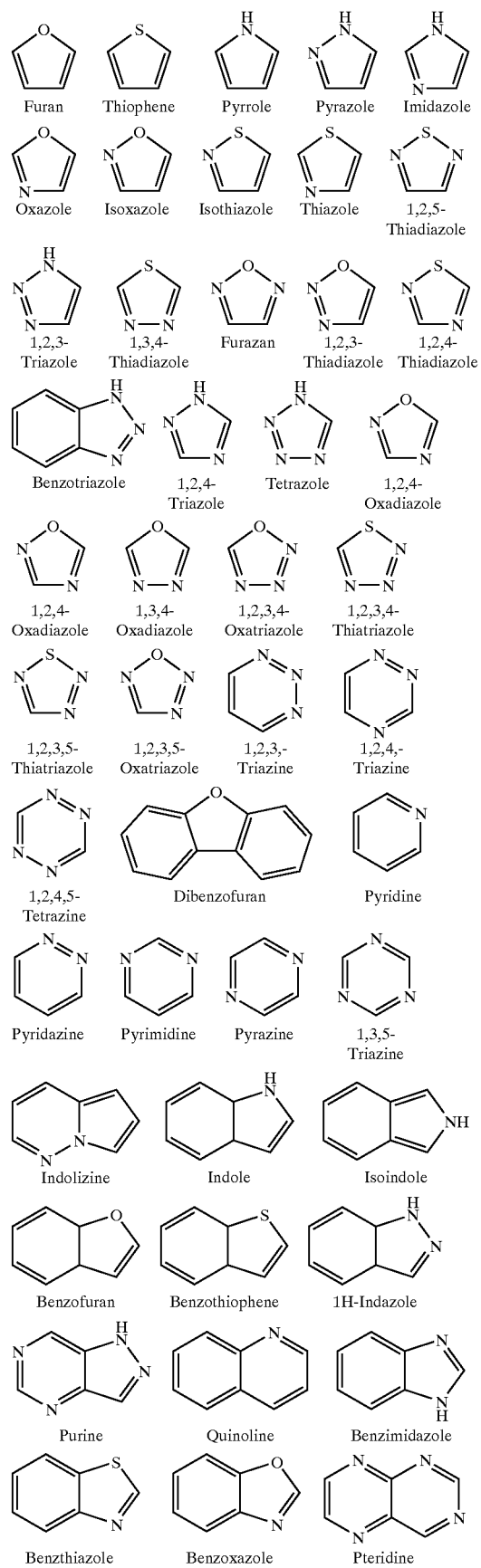

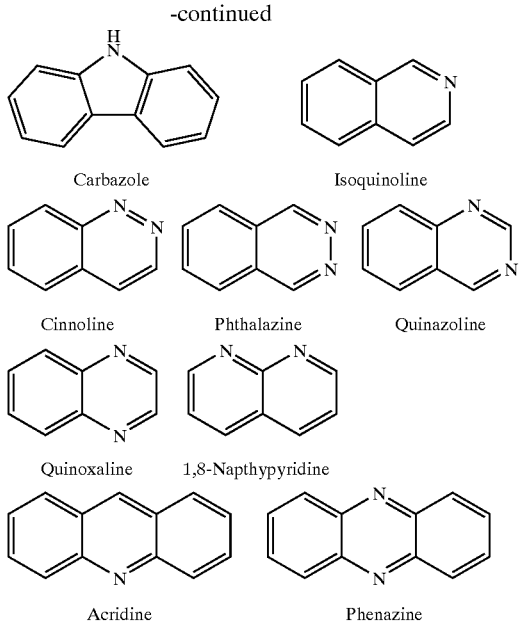

Heteroaryl rings may be unsubstituted or substituted with from 1 to 4, preferably from 1 to 3, more preferably from 1 to 2, substituents on the ring. Preferred heteroaryl rings are unsubstituted or substituted with 1 or 2 substituents. Heteroaryl rings may be substituted with halo, cyano, nitro, hydroxy, amino, alkyl, lower alkenyl, lower alkynyl, heteroalkyl, aryloxy, alkoxy, methylenedioxy, thioalkoxy, thioaryloxy, or any combination thereof. Preferred heteroaryl ring substituents include halo, cyano, amino, alkyl, heteroalkyl, aryloxy, alkoxy, methylenedioxy, thioalkoxy, thioaryloxy.

"Heteroatom" refers to a nitrogen, sulfur, or oxygen atom. Groups containing more than one heteroatom may contain different heteroatoms.

"Heterocycloalkyl" is a saturated ring containing carbon atoms and from 1 to 4, preferably 1 to 3, heteroatoms in the ring. Heterocycloalkyl rings are not aromatic. Heterocycloalkyl rings are monocyclic, or are fused, bridged, or spiro polycyclic ring systems. Monocyclic heterocycloalkyl rings contain from 3 to 9 member atoms (carbon and heteroatoms), preferably from 5 to 7 member atoms, in the ring. Polycyclic heterocycloalkyl rings contain from 7 to 17 member atoms, preferably 7 to 12 member atoms, in the ring. Preferred polycyclic heterocycloalkyl rings comprise 5-, 6- or 7-membered rings fused to 5-, 6-, or 7-membered rings. Preferred heterocycloalkyl rings include but are not limited to the following:

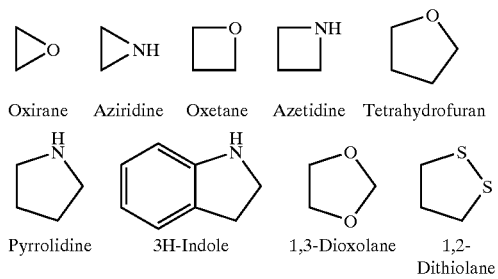

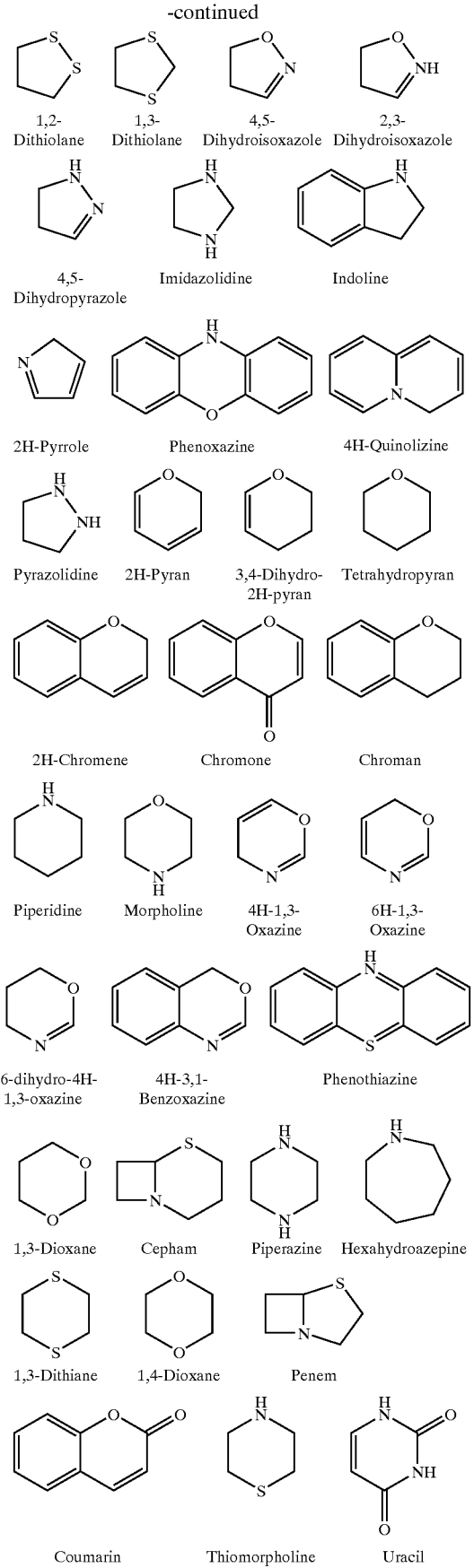

-continued

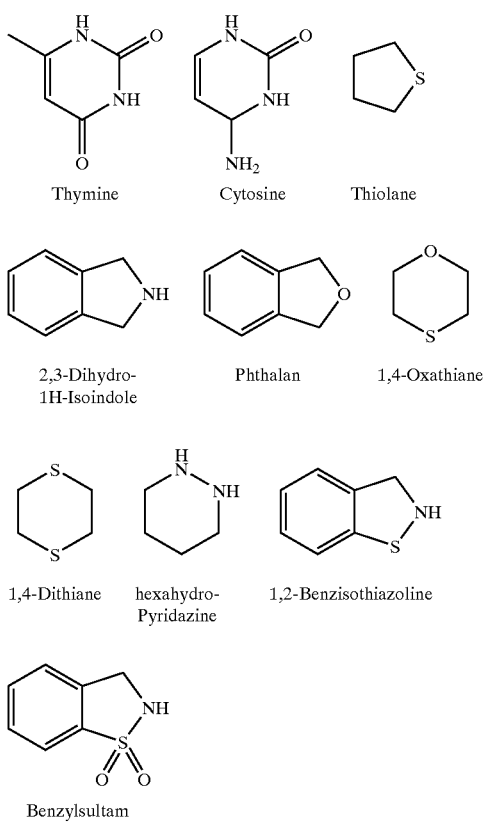

Thymine    Cytosine    Thiolane 2,3-Dihydro-    Phthalan    1,4-Oxathiane
1H-Isoindole 1,4-Dithiane    hexahydro-    1,2-Benzisothiazoline
Pyridazine Benzylsultam Heterocycloalkyl rings may be unsubstituted or substituted with from 1 to 4 substituents on the ring. Heterocycloalkyl group substituents include alkyl, aryl (e.g., phenyl), alkoxy, aryloxy (e.g., phenoxy), thioalkoxy, thioaryloxy, heteroaryl, cycloalkyl, halo, hydroxy, amino, keto, thioketo, nitro, and cyano. Preferred heterocycloalkyl group substituents include alkyl, aryl (e.g., phenyl), alkoxy, aryloxy (e.g., phenoxy), heteroaryl, halo, hydroxy, amino, and keto.

"Keto" refers to the group =O.

"Nitro" refers to the group —NO$_2$.

"Optical isomer", "stereoisomer", and "diastereomer" as referred to herein have the standard art recognized meanings (see, e.g., *Hawley's Condensed Chemical Dictionary*, 11th Ed.). The illustration of derivatives of the compounds of the instant invention is not intended to be limiting. The application of useful protecting groups, salt forms, etc. is within the ability of the skilled artisan.

A "pharmaceutically-acceptable salt" is a cationic salt formed at any acidic (e.g., carboxylic acid) group, or an anionic salt formed at any basic (e.g., amino) group. Many such salts are known in the art, as described in World Patent Publication 87/05297, Johnston et al., published Sep. 11, 1987 incorporated by reference herein. Preferred cationic salts include the alkali metal salts (such as sodium and potassium), and alkaline earth metal salts (such as magnesium and calcium) and organic salts. Preferred anionic salts include the halides (such as chloride salts), sulfonates, carboxylates, phosphates, and the like. Clearly contemplated in such salts are addition salts that may provide an optical center where once there is none. For example, a chiral tartrate salt may be prepared from the compounds of the invention, and this definition includes such chiral salts.

Such salts are well understood by the skilled artisan, and the skilled artisan is able to prepare any number of salts given the knowledge in the art. Furthermore, it is recognized that the skilled artisan may prefer one salt over another for reasons of solubility, stability, formulation ease and the like. Determination and optimization of such salts is within the purview of the skilled artisan's practice.

"Thioalkoxy" refers to the group —S(O)$_{0-2}$R where R is alkyl, alkenyl, alkynyl, heteroalkyl, heteroalkenyl, heteroalkynyl, cycloalkyl, cycloalkenyl, or heterocycloalkyl. Preferred thioalkoxy groups include methanesulfonyl.

"Thioaryloxy" refers to the group —S(O)$_{0-2}$R where R is aryl or heteroaryl. Preferred thioaryloxy groups include phenylsulfide, benzenesulfonyl and pyridinesulfonyl.

"Thioketo" refers to the group =S.

Compounds

The invention is directed to compounds of Formula (I):

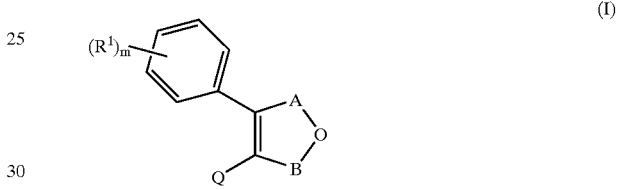

(I)

In the above structure, each $R^1$ is independently selected from the group consisting of: lower alkyl, lower alkenyl, lower alkynyl, lower heteroalkyl, lower heteroalkenyl, lower heteroalkynyl, heterocycloalkyl, heteroaryl, halo, CN, OR$^4$, SR$^4$, S(O)R$^4$, S(O)$_2$R$^4$, and NR$^4$R$^5$. Preferred $R^1$ is lower alkyl, halo, CN, OR$^4$, and NR$^4$R$^5$. More preferred $R^1$ is lower alkyl, halo, and CN.

In the above structure, m is an integer from 0 to 5. Preferred m is 0 to 3. More preferred m is 1 or 2.

In the above structure, Q is selected from the group consisting of

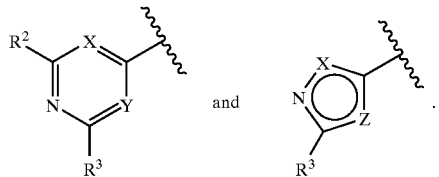

Each $R^2$ is independently selected from the group consisting of: H, alkyl, alkenyl, alkynyl, heteroalkyl, heteroalkenyl, heteroalkynyl, heterocycloalkyl, heteroaryl, halo, OH, CN, OR$^4$, SR$^4$, S(O)R$^4$, S(O)$_2$R$^5$, and NR$^4$R$^5$. Preferred $R^2$ is H, and halo. More preferred $R^2$ is H.

$R^3$ is selected from the group consisting of: H, alkyl, alkenyl, alkynyl, heteroalkyl, heteroalkenyl, heteroalkynyl, heterocycloalkyl, heteroaryl, halo, OH, CN, OR$^4$, SR$^4$, S(O)R$^4$, and S(O)$_2$R$^4$. Preferred $R^3$ is H, alkyl, halo, OR$^4$, NR$^4$R$^5$, SR$^4$, S(O)R$^4$, S(O)$_2$R$^4$. More preferred $R^3$ is H, OR$^4$, NR$^4$R$^5$.

X is selected from the group consisting of: $CR^3$ and N. Preferred X is $CR^2$. The most preferred X is CH.

Y is selected from the group consisting of: $CR^2$ and N. Preferred Y is CH and N.

Z is selected from the group consisting of $NR^4$, O, and S.

In the above structure, A is selected from the group consisting of: C(O) and N-G.

In the above structure, B is selected from the group consisting of: C(O) and N-G.

Provided that one and only one of A or B is C(O).

In the above structure, G is selected from the group consisting of H, alkyl, alkenyl, alkynyl, cycloalkyl, cycloalkenyl, cycloalkynyl, aryl, heteroalkyl, heteroalkenyl, heteroalkynyl, heterocycloalkyl, heteroaryl, $OR^4$, $S(O)_2R^4$. Preferred G is alkyl, alkynyl, aryl, heteroalkyl, heteroalkynyl, heterocycloalkyl, heteroaryl, $OR^4$, $S(O)_2R^4$. More preferred G is substituted alkyl (wherein the preferred substituents are keto, alkoxy, aryloxy, amino, heteroaryl, heterocycloalkyl) and aryl.

Each $R^4$ is independently selected from H, lower alkyl, lower alkenyl, lower alkynyl, cycloalkyl, cycloalkenyl, aryl, heteroalkyl, heteroalkenyl, heteroalkynyl, heterocycloalkyl, heterocycloalkenyl, and heteroaryl. Preferred $R^4$ is H, lower alkyl, heteroalkyl, aryl, and heteroaryl.

Each $R^5$ is independently selected from H, lower alkyl, lower alkenyl, lower alkynyl, cycloalkyl, cycloalkenyl, aryl, heteroalkyl, heteroalkenyl, heteroalkynyl, heterocycloalkyl, heterocycloalkenyl, heteroaryl, $OR^4$, and $S(O)_2R^4$. Preferred $R^5$ is H, lower alkyl, and $S(O)_2R^4$.

While alkyl, heteroalkyl, cycloalkyl, and heterocycloalkyl groups may be substituted with hydroxy and amino groups as stated above, the following are not envisioned in the invention:

1. Enols (OH attached to a carbon bearing a double bond).
2. Amino groups attached to a carbon bearing a double bond (except for vinylogous amides).
3. More than one hydroxy, amino, or amido attached to a single carbon (except where two nitrogen atoms are attached to a single carbon atom and all three atoms are member atoms within a heterocycloalkyl ring).
4. Hydroxy, amino, or amido attached to a carbon that also has a heteroatom attached to it.
5. Hydroxy, amino, or amido attached to a carbon that also has a halogen attached to it.

Compound Preparation

The compounds of the invention can be prepared using conventional organic syntheses. Particularly preferred syntheses are carried out according to the following general reaction schemes, Schemes 1, 2, 3, 4 and 5. Scheme 1 describes a general reaction scheme for making compounds of the invention wherein "A" is C(O) and "Q" is either a 5- or 6-membered heteroaryl ring. Scheme 2 describes a general reaction scheme for making compounds of the invention wherein "A" is C(O) and "Q" is a specifically a 6-membered heteroaryl ring. Scheme 3 describes a general reaction scheme for making compounds of the invention wherein "B" is C(O) and "Q" is either a 5- or 6-membered heteroaryl ring. Scheme 4 describes a general reaction scheme for making compounds of the invention wherein "A" is C(O) and "Q" is specifically a 5-membered ring. Scheme 5 describes a general reaction scheme for making compounds of the invention wherein "A" is C(O), "Q" is 5- or 6-membered heteroaryl ring, and "G" is a heteroalkyl substituent.

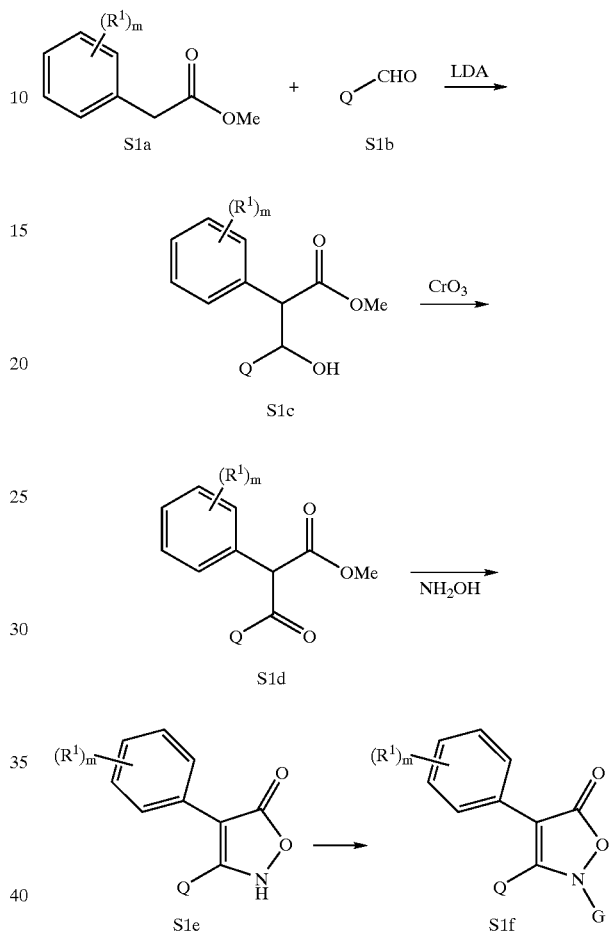

In Scheme 1, $R^1$, m, G and Q are as defined above. Substituted heterocycles of type S1b and esters of type S1a are either commercially available as starting material or are made from commercially available starting materials using methods known to one of ordinary skill in the art. Coupling of S1a with S1b to form β-hydroxyester S1c is accomplished using the method described by Smith, A. B. III et al. (*Synthesis* 1981, 567–570). Oxidation of alcohol S1c with chromium (VII) oxide provides ketone S1d. Cyclocondensation of β-ketoester S1d with hydroxylamine is carried out at 90° C. in pyridine to give the disubstituted isoxazolone S1e. Elaboration of isoxazolone S1e is accomplished under a variety of conditions to provide access to a wide variety of functionalized isoxazolones of type S1f. For example, acylation of S1e with acyl halides and tertiary amine base gives amides. Reaction of S1e with carbamoyl chlorides gives ureas. Copper-mediated coupling of S1e with aryl boronic acids gives aryl amines. Reaction of S1e with sulfonyl chlorides and tertiary amine bases gives sulfonamides.

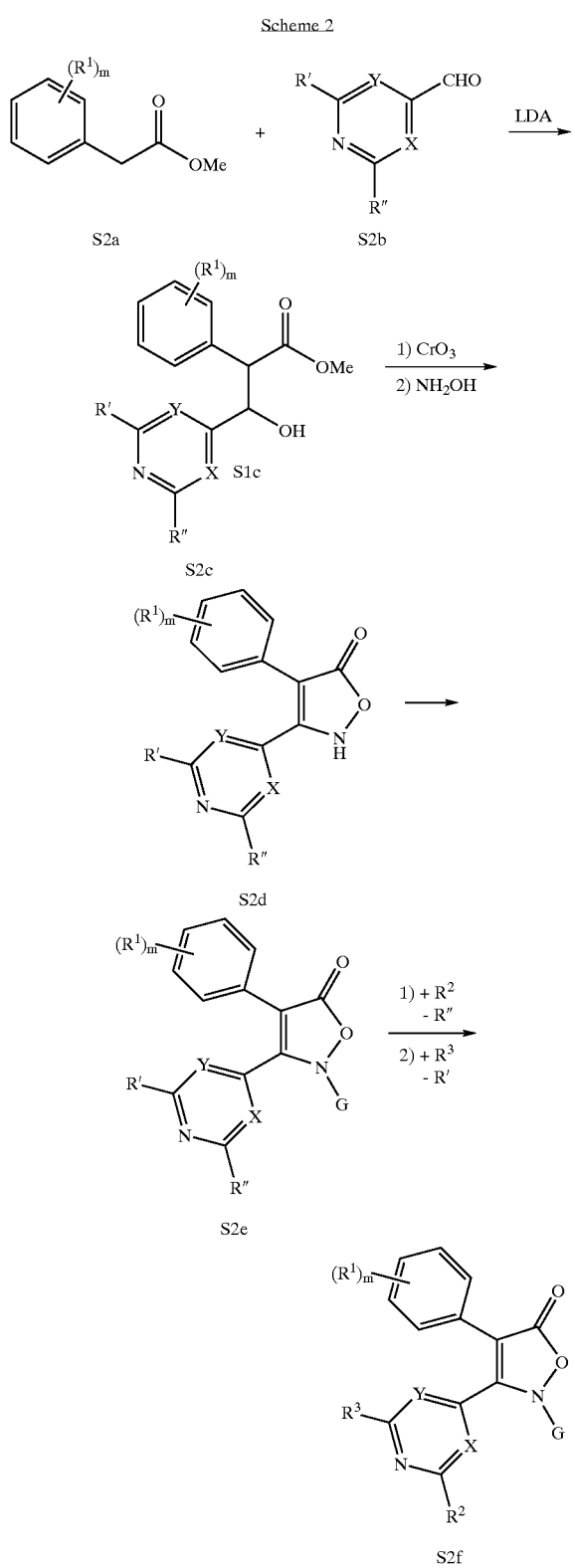

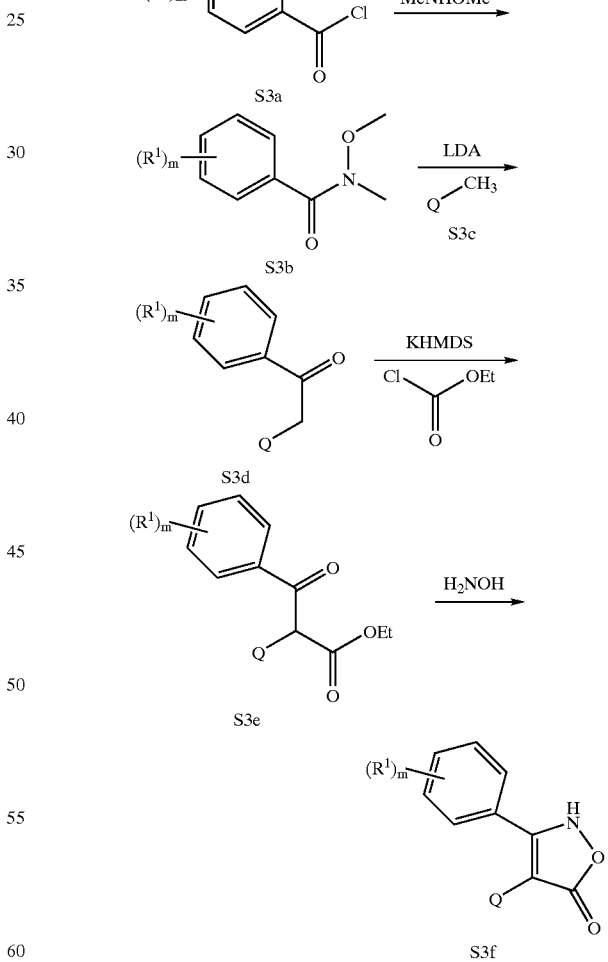

two approaches are used. In the first approach, isoxazolones of type S2d are substituted at the isoxazolone nitrogen position as described in Scheme 1 to give S2e. When either R' or R" is —SMe, isoxazolone S2d is oxidized specifically to either the corresponding sulfoxide or the sulphone (not shown) with several different commonly-used reagents (e.g., peracetic acid, 3-chloroperbenzoic acid, or potassium peroxymonosulfate). Either the sulfoxide or the corresponding sulphone is then displaced under nucleophilic conditions to give compounds of type S2f. In the second approach, S2d (where R' and/or R" is —SMe) is first oxidized specifically to either the sulfoxide or the sulphone. The sulfoxide or the sulphone then undergoes nucleophilic substitution (replacement of R' for $R^3$ and/or R" for $R^2$), followed by the previously described electrophilic substitution of the isoxazolone ring to give compounds of type S2f. Using either approach, R' and/or R" may be —SMe, halo, or some other substituent capable of being displaced by $R^2$ or $R^3$. Furthermore, use of halo for R' and/or R" precludes the additional step of oxidizing the respective R' and/or R" to a better leaving group.

In Scheme 2, $R^1$, $R^2$, $R^3$, m, G, X, and Y are as defined above. R' and R" are each appropriate functional groups which enable the skilled artisan to functionalize the six-membered heterocycle to ultimately form a compound according to the invention. To further elaborate the isoxazolone scaffold, R' and R" on S2d may be exchanged for a wide variety of functional groups ($R^2$ and $R^3$). In practice In Scheme 3, $R^1$, m and Q are as defined above. Substituted heterocyclic amides S3b are readily prepared from commercially available acid chlorides of type S3a. Coupling of S3b and 6-membered heterocycles of type S3c to form S3d is accomplished using a known method (Liverton, N. J. et. al. *J. Med. Chem.* 1999, 42, 2180–2190). An analogous coupling of S3b and 5-membered heterocycles of type S3c is accomplished using similar methods (oxazoles: see Evans, D. A., Cee, V. J., Smith, T. E., Santiago, K. J. *Org. Lett.* 1999, 1, 87–90; imidazoles: see *Heterocycles*, 1989, 29, 1551–1558). Deprotonation of ketone S3d with potassium bis(trimethylsilyl)amide ("KHMDS") and quenching of the resulting enolate with ethylchloroformate provides β-ketoester S3e. Cyclocondensation of β-ketoester S3e with hydroxylamine provides the disubstituted isoxazolone of type S3f. Elaboration of isoxazolone S3f is accomplished according to previously mentioned procedures.

starting material or are made from commercially available starting materials using methods disclosed in the literature (see Shafer, C. M. *J. Org. Chem.* 1998, 63, 551–555 and references therein). Coupling of S4a and S4b to form S4c followed by oxidation and cyclocondensation with hydroxylamine to give S4d is accomplished as described in Schemes 1 and 2. Oxidation to sulfone S4e using literature procedure is followed by elaboration of the isoxazolone scaffold to S4f as described in Scheme 2.

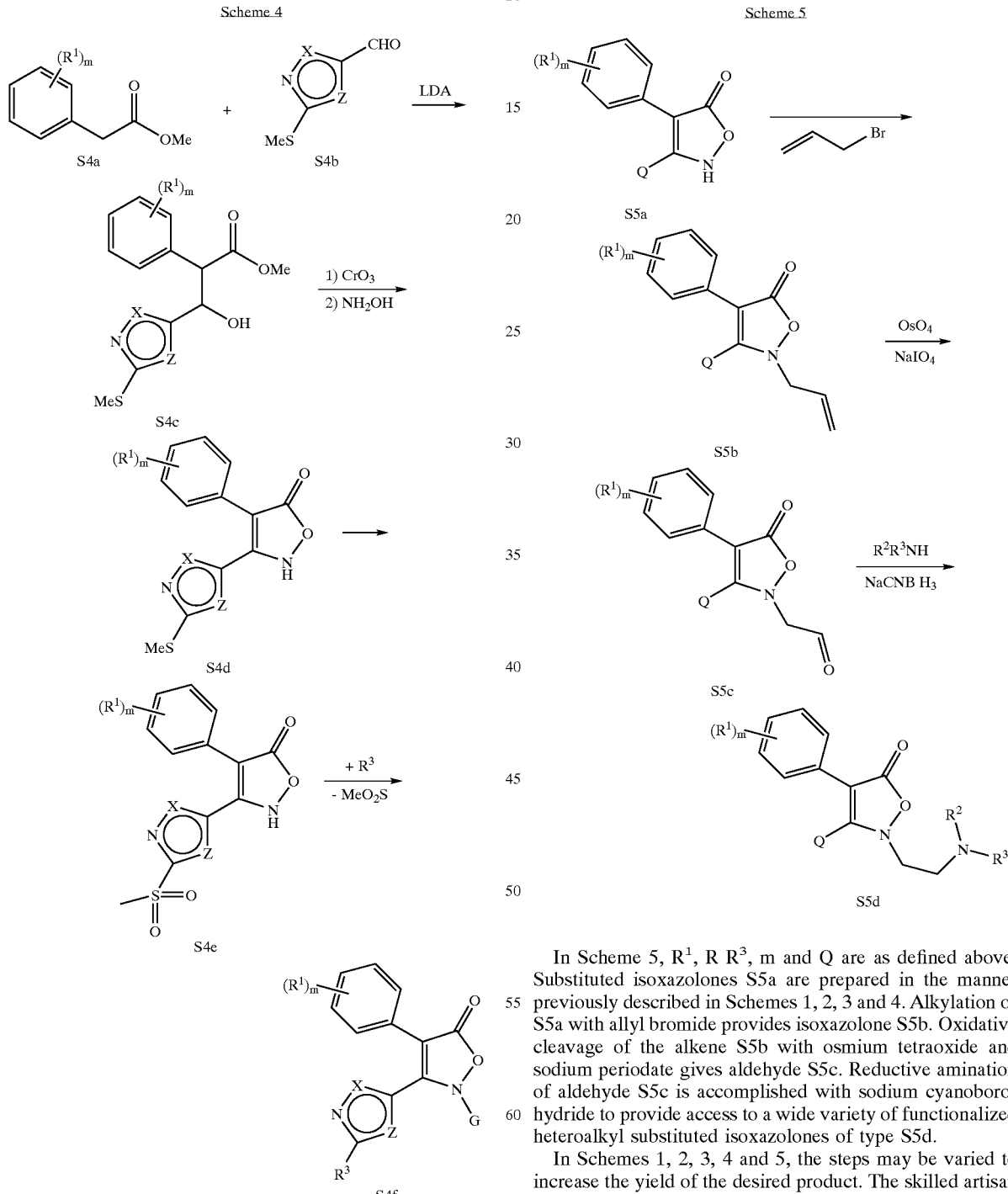

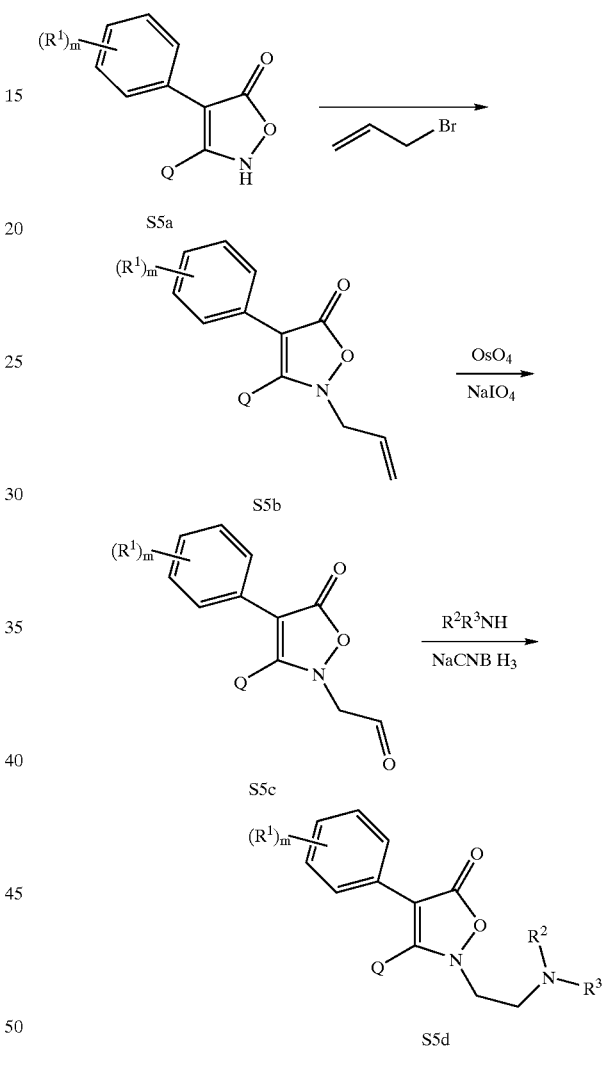

In Scheme 4, $R^1$, $R^3$, m, G, X, and Z are as defined above. Aldehydes of type S4b are either commercially available as In Scheme 5, $R^1$, $R^2$ $R^3$, m and Q are as defined above. Substituted isoxazolones S5a are prepared in the manner previously described in Schemes 1, 2, 3 and 4. Alkylation of S5a with allyl bromide provides isoxazolone S5b. Oxidative cleavage of the alkene S5b with osmium tetraoxide and sodium periodate gives aldehyde S5c. Reductive amination of aldehyde S5c is accomplished with sodium cyanoborohydride to provide access to a wide variety of functionalized heteroalkyl substituted isoxazolones of type S5d.

In Schemes 1, 2, 3, 4 and 5, the steps may be varied to increase the yield of the desired product. The skilled artisan will recognize the judicious choice of reactants, solvents, and temperatures is an important component in any successful synthesis. Determination of optimal conditions, solvents, reaction times, and amounts is routine. Thus the skilled artisan can make a variety of compounds using the guidance of the schemes above.

It is recognized that the skilled artisan in the art of organic chemistry can readily carry out standard manipulations of organic compounds without further direction; that is, it is well within the scope and practice of the skilled artisan to carry out such manipulations. These include, but are not limited to, reduction of carbonyl compounds to their corresponding alcohols, oxidations of hydroxyls and the like, acylations, aromatic substitutions, both electrophilic and nucleophilic, etherifications, esterification and saponification and the like. Examples of these manipulations are discussed in standard texts such as March, *Advanced Organic Chemistry* (Wiley), Carey and Sundberg, *Advanced Organic Chemistry* (Vol. 2) and other art that the skilled artisan is aware of.

The skilled artisan will also readily appreciate that certain reactions are best carried out when another potentially reactive functionality on the molecule is masked or protected, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene, *Protecting Groups in Organic Synthesis*. Of course, amino acids used as starting materials with reactive side chains are preferably blocked to prevent undesired side reactions.

The compounds of the invention may have one or more chiral centers. As a result, one may selectively prepare one optical isomer, including diastereomer and enantiomer, over another, for example by chiral starting materials, catalysts or solvents, or may prepare both stereoisomers or both optical isomers, including diastereomers and enantiomers at once (a racemic mixture). Since the compounds of the invention may exist as racemic mixtures, mixtures of optical isomers, including diastereomers and enantiomers, or stereoisomers may be separated using known methods, such as chiral salts, chiral chromatography and the like.

In addition, it is recognized that one optical isomer, including diastereomer and enantiomer, or stereoisomer may have favorable properties over the other. Thus when disclosing and claiming the invention, when one racemic mixture is disclosed, it is clearly contemplated that both optical isomers, including diastereomers and enantiomers, or stereoisomers substantially free of the other are disclosed and claimed as well.

EXAMPLES

The following non-limiting examples illustrate the compounds of the present invention and the methods for preparing these compounds. Compounds are analyzed using $^1$H and $^{13}$C NMR, elemental analysis, mass spectra and/or infrared spectra, as appropriate.

All solvents are purchased as the appropriate grade, and reactions are performed under an inert nitrogen atmosphere, unless otherwise noted. Chromatography is performed on silica gel (70–230 mesh; Aldrich) or (230–400 mesh; Merck) as appropriate. Thin layer chromatography analysis (TLC) is performed on glass mounted silica gel plates (200–300 mesh; Baker) and visualized with UV or 5% phosphomolybdic acid in ethanol (EtOH).

The following abbreviations are used herein:
MeOH: methanol
EtOAc: ethylacetate
Ph: phenyl
Ac: acetate
DMF: N,N-dimethylformamide
d: day(s)
LDA: lithium diisopropylamide
PMB: para-methoxybenzyl
KHMDS: potassium bis(trimethylsilyl)amide
BOC: tert-butyloxycarbonyl
MCPBA: meta-chloroperbenzoic acid
LC/MS: liquid chromatography/mass spectroscopy
prep HPLC.: preparative-scale high pressure liquid chromatography
Et$_3$N: triethylamine
Et$_2$O: diethylether
conc: concentrated
TLC: thin layer chromatography
h: hour(s)
min: minute(s)

Example 1

2-Ethoxymethyl-4-(4-fluorophenyl)-3-pyridin-4-yl-2H-isoxazol-5-one a) 2-(4-Fluorophenyl)-3-hydroxy-3-pyridin-4-yl-propionic acid methyl ester

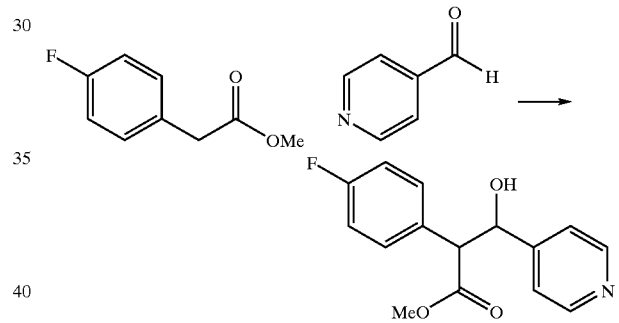

Commercially-available 4-fluorophenylmethylacetate and 4-pyridine-carboxaldehyde are reacted according to published procedure (Smith, A. B. III; Levenberg, P. A. *Synthesis* 1981, 567–570) to give the desired alcohol 1a.

b) 2-(4-Fluorophenyl)-3-oxo-3-pyridin-4-yl-propionic acid methyl ester

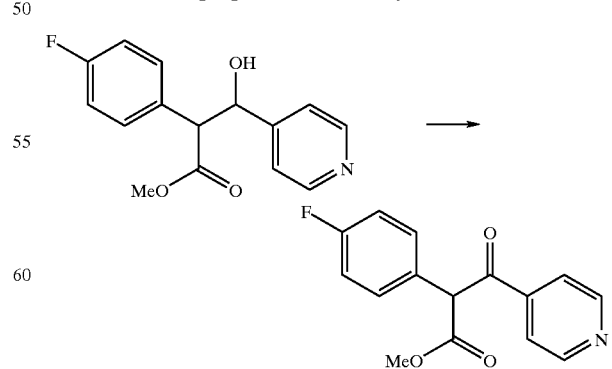

To a stirred suspension of chromium (VI) oxide (13.2 g, 130.9 mmols) in CH$_2$Cl$_2$ (400 mL) is added pyridine (10.6 mL, 261.6 mmols). The reaction mixture is stirred for 1 h at room temperature. A solution of alcohol 1a (6.0 g, 21.8 mmol) in CH₂Cl₂ (50 mL) is added dropwise, and the reaction mixture is stirred for 24 h at room temperature. The mixture is diluted with ether (800 mL) and filtered through celite. The filtrate is concentrated under reduced pressure to give a brown oil. Purification by flash chromatography (50% EtOAc: Hexanes) gives ketone 1b as a light-colored thick oil. Using substantially the same procedure, substituting the appropriate starting material, many other β-ketoester intermediates can be made.

The following intermediates identified in Table 1 are prepared according to the method described immediately above substituting the appropriate starting materials.

TABLE 1

| Example | Structure |
|---------|-----------|
| 1c | 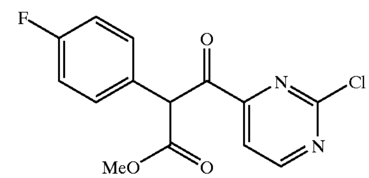 |
| 1d | 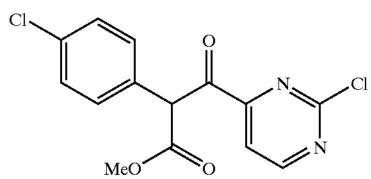 |
| 1e | 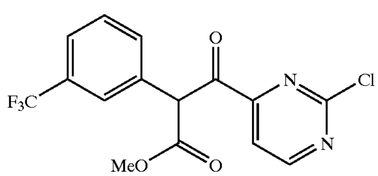 |
| 1f | 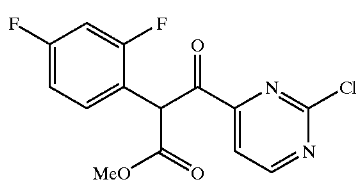 |
| 1g | 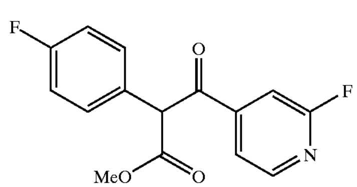 |
| 1h | 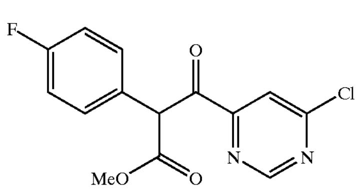 |
| 1i | |
| 1j | |
| 1k | | l) 4-(4-Fluorophenyl)-3-pyridin-4-yl-2H-isoxazol-5-one

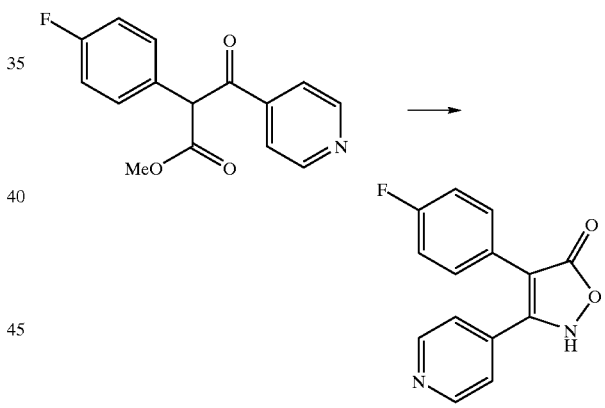

A solution of ketone 1b (24.0 g, 0.09 mol) and N,O-dimethylhydroxylamine hydrochloride (9.7 g, 0.14 mol) in pyridine (200 mL) is heated for 4 h at 90° C. The solution is concentrated under reduced pressure to give a semisolid residue, which is diluted with aqueous saturated NaHCO₃ solution and washed with EtOAc two times. The aqueous phase is concentrated under reduced pressure. The resulting yellow solid is washed with MeOH, filtered and the filtrate conc to dryness. The crude isoxazolone 1l is used without further purification in the following step.

The following compounds identified in Table 2 are prepared analogously to Example 1l using the appropriately functionalized hydroxylamines.

TABLE 2

| Example | Structure | Compound Name |
|---|---|---|
| 2 | 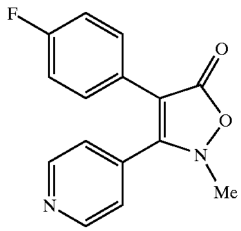 | 4-(4-Fluorophenyl)-2-methyl-3-pyridin-4-yl-2H-isoxazol-5-one |
| 3 | 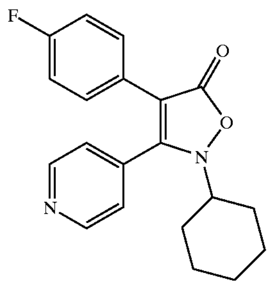 | 2-Cyclohexyl-4-(4-fluorophenyl)-3-pyridin-4-yl-2H-isoxazol-5-one |
| 4 | 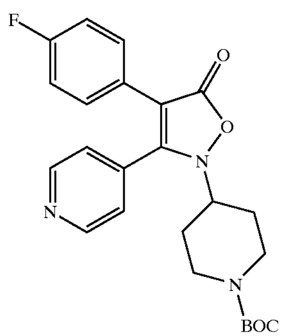 | 4-(4-Fluorophenyl)-2-[4-(tert-butylcarbonyl)-4-piperidinyl]-3-pyridin-4-yl-2H-isoxazol-5-one |
| 5 | | 4-(4-Fluorophenyl)-3-[2-(4-methoxybenzyl)-oxazol-4-yl]-2H-isoxazol-5-one | m) 2-Ethoxymethyl-4-(4-fluorophenyl)-3-pyridin-4-yl-2H-isoxazol-5-one

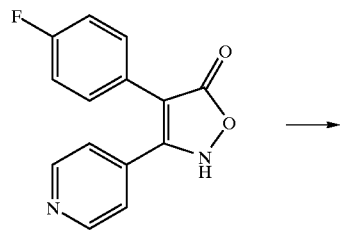

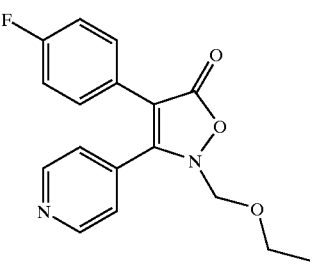

To a solution of isoxazolone 1l (0.25 g, 0.97 mmol) and Et$_3$N (0.15 mL, 1.07 mmol) in CH$_2$Cl$_2$ (4 mL) is added chloromethylethyl ether (0.10 mL, 1.07 mmol). The reaction mixture is stirred for 16 h at room temperature. The mixture is diluted with aqueous saturated NaHCO$_3$ and extracted with EtOAc two times. The combined organic layers are dried over MgSO$_4$, filtered and concentrated under reduced pressure. Purification by flash chromatography (33% EtOAc: Hexanes) gives isoxazolone 1m as a yellow residue.

The following compounds of Formula 4a identified in Table 3 are prepared analogously to Example 1m.

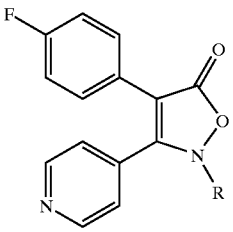

4a

| Example | R | Compound Name |
|---|---|---|
| 6 | 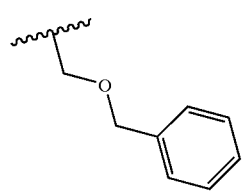 | 2-(2-Chloro-ethoxymethyl)-4-(4-fluorophenyl)-3-pyridin-4-yl-2H-isoxazol-5-one |
| 7 | | 2-Benzyloxymethyl-4-(4-fluorophenyl)-3-pyridin-4-yl-2H-isoxazol-5-one |
| 8 |  | 4-(4-Fluorophenyl)-2-(2-methoxy-ethoxymethyl)-3-pyridin-4-yl-2H-isoxazol-5-one |

-continued

| Example | R | Compound Name |
|---|---|---|
| 9 | ~~~CH2-OMe | 4-(4-Fluorophenyl)-2-methoxymethyl-3-pyridin-4-yl-2H-isoxazol-5-one |
| 10 | ~~~CH2-O-C(=O)-C(CH3)3 | 4-(4-Fluorophenyl)-2-pivalyloxymethyl-3-pyridin-4-yl-2H-isoxazol-5-one |

Example 11
4-(4-Fluorophenyl)-2-(morpholine-4-carbonyl)-3-pyridin-4-yl-2H-isoxazol-5-one

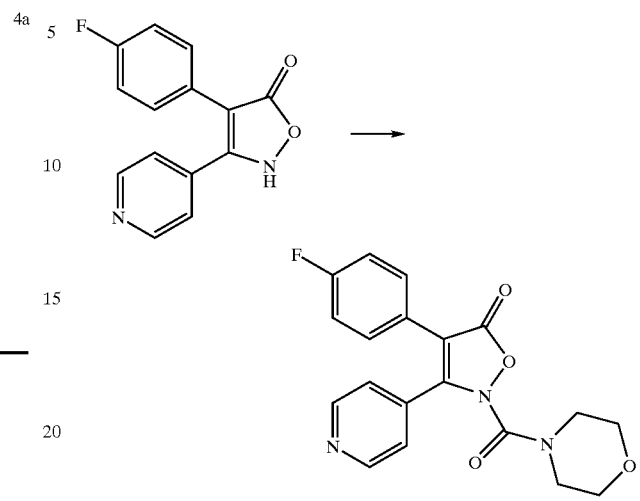

To a solution of isoxazolone 11 (0.25 g, 0.97 mmol) and $Et_3N$ (0.15 mL, 1.07 mmol) in $CH_2Cl_2$ (4 mL) is added 4-morpholine carbomoyl chloride (0.22 mL, 1.94 mmol) The reaction mixture is stirred for 16 h at room temperature. The mixture is diluted with aqueous saturated $NaHCO_3$ and extracted with EtOAc two times. The combined organic layers are dried over $MgSO_4$, filtered and concentrated under reduced pressure. Purification by flash chromatography (33% EtOAc: Hexanes) gives isoxazolone 11 as a yellow residue.

The following compounds of Formula 4a identified in Table 4 are prepared analogously to Example 11.

TABLE 4

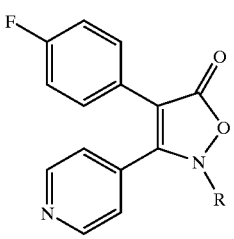

4a

| Example | R | Compound Name |
|---|---|---|
| 12 | ~~~C(=O)-N(piperazine)N-CH3 | 4-(4-Fluorophenyl)-2-(4-methylpiperazine-1-carbonyl)-3-pyridin-4-yl-2H-isoxazol-5-one |
| 13 | ~~~C(=O)-N(piperazine)N-C(=O)-O-CH2-Ph | 4-(4-Fluorophenyl)-2-[4-(benzyloxycarbonyl)piperazine-1-carbonyl]-3-pyridin-4-yl-2H-isoxazol-5-one |

TABLE 4-continued

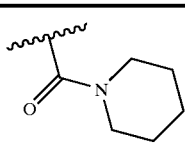

| Example | R | Compound Name |
|---|---|---|
| 14 | 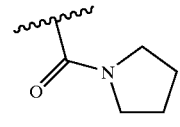 | 4-(4-Fluorophenyl)-2-(piperidine-4-carbonyl)-3-pyridin-4-yl-2H-isoxazol-5-one |
| 15 | 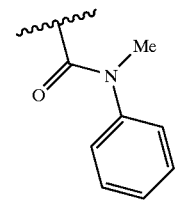 | 4-(4-Fluorophenyl)-2-(pyrrolidine-4-carbonyl)-3-pyridin-4-yl-2H-isoxazol-5-one |
| 16 | 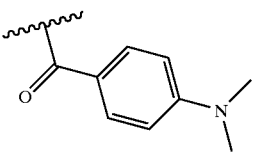 | 4-(4-Fluorophenyl)-5-oxo-3-pyridin-4-yl-5H-isoxazol-2-carboxylic acid methylphenyl amide |
| 17 | 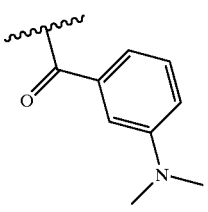 | 2-(4-Dimethylaminobenzoyl)-4-(4-fluorophenyl)-3-pyridin-4-yl-2H-isoxazol-5-one |
| 18 | 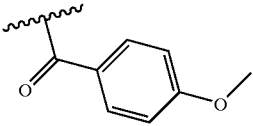 | 2-(3-Dimethylaminobenzoyl)-4-(4-fluorophenyl)-3-pyridin-4-yl-2H-isoxazol-5-one |
| 19 | 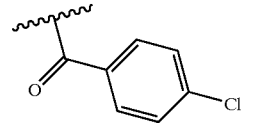 | 4-(4-Fluorophenyl)-2-(4-methoxyphenyl-carbonyl)-3-pyridin-4-yl-2H-isoxazol-5-one |
| 20 | 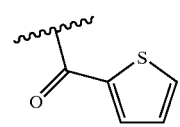 | 2-(4-Chloro)-4-(4-fluorophenyl)-3-pyridin-4-yl-2H-isoxazol-5-one |
| 21 |  | 4-(4-Fluorophenyl)-3-pyridin-4-yl-2-(thiophen-2-ylcarbonyl)-2H-isoxazol-5-one |

TABLE 4-continued

| Example | R | Compound Name |
|---|---|---|
| 22 | (furan-2-ylcarbonyl) | 4-(4-Fluorophenyl)-2-(4-furan-2-ylcarbonyl)-3-pyridin-4-yl-2H-isoxazol-5-one |
| 23 | (methylcarbonyl) | 4-(4-Fluorophenyl)-2-(4-methylcarbonyl)-3-pyridin-4-yl-2H-isoxazol-5-one |
| 24 | (ethoxycarbonyl) | 2-Ethoxycarbonyl-4-(4-fluorophenyl)-3-pyridin-4-yl-2H-isoxazol-5-one |
| 25 | (benzyloxycarbonyl) | 4-(4-Fluorophenyl)-2-phenylmethoxycarbonyl-3-pyridin-4-yl-2H-isoxazol-5-one |
| 26 | (phenylthio-thiocarbonyl) | 4-(4-Fluorophenyl)-2-(4-phenylthio-thiocarbonyl)-3-pyridin-4-yl-2H-isoxazol-5-one |
| 27 | (phenylsulfonyl) | 4-(4-Fluorophenyl)-2-phenylsulfonyl-3-pyridin-4-yl-2H-isoxazol-5-one |
| 28 | (4-methoxyphenylsulfonyl) | 4-(4-Fluorophenyl)-2-(4-methoxyphenylsulfonyl)-3-pyridin-4-yl-2H-isoxazol-5-one |

TABLE 4-continued

| Example | R | Compound Name |
|---|---|---|
| 29 | -S(=O)₂-C₆H₄-S(=O)₂-CH₃ | 4-(4-Fluorophenyl)-2-(4-(methylsulfonyl)phenylsulfonyl)-3-pyridin-4-yl 2H-isoxazol-5-one |

Example 30

2-Benzyl-4-(4-fluorophenyl)-3-pyridin-4-yl-2H-isoxazol-5-one

To a solution of isoxazolone 11 (0.40 g, 1.56 mmol) and Et₃N (0.87 mL, 6.24 mmol) in DMF (8 mL) is added benzyl bromide (0.56 mL, 4.65 mmol) followed by tetrabutylammonium iodide (0.28 g, 0.78 mmol). The reaction mixture is stirred for 16 h at room temperature. The mixture is diluted with aqueous saturated NaHCO₃ and extracted with EtOAc two times. The combined organic layers are dried over MgSO₄, filtered and concentrated under reduced pressure. Purification by prep HPLC gives isoxazolone 30 as a yellow residue.

The following compounds of Formula 4a identified in Table 6 are prepared analogously to Example 30.

TABLE 6

| Example | R | Compound Name |
|---|---|---|
| 31 | allyl | 2-(Allyl)-4-(4-fluorophenyl)-3-pyridin-4-yl-2H-isoxazol-5-one |
| 32 | 4-methoxybenzyl | 4-(4-fluorophenyl)-2-(4-methoxybenzyl)-3-pyridin-4-yl-2H-isoxazol-5-one |
| 33 | 3-nitrobenzyl | 4-(4-fluorophenyl)-2-(3-nitrobenzyl)-3-pyridin-4-yl-2H-isoxazol-5-one |
| 34 | 4-cyanobenzyl | 4-(4-fluorophenyl)-2-(4-tolunitrile)-3-pyridin-4-yl-2H-isoxazol-5-one |

TABLE 6-continued

| Example | R | Compound Name |
|---|---|---|
| 35 | (benzyl with OCF₃ para) | 4-(4-fluorophenyl)-3-pyridin-4-yl-2-(4-trifluoromethoxybenzyl)-2H-isoxazol-5-one |
| 36 | (benzyl with CF₃ para) | 4-(4-fluorophenyl)-3-pyridin-4-yl-2-(4-trifluoromethylbenzyl)-2H-isoxazol-5-one |

Example 37

2-(2,4-Dimethoxyphenyl)-4-(4-fluorophenyl)-3-pyridin-4-yl-2H-isoxazol-5-one

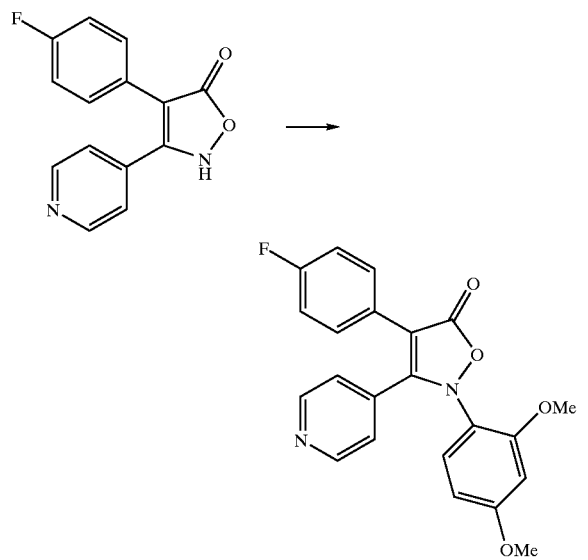

To a stirred solution of isoxazolone 11 (0.25 g, 0.97 mmol) in CH$_2$Cl$_2$ (10 mL) is added 2,4-dimethoxyphenylboronic acid (0.36 g, 1.95 mmol), Cu(OAc)$_2$ (0.76 g, 1.46 mmol), pyridine (0.16 mL, 1.95 mmol) and 4 Å molecular sieves (0.75 g). The reaction is stirred 22 h and then filtered through a bed of celite. The filtrate is concentrated under reduced pressure to give the crude product, which is purified by flash chromatography (66% EtOAc: Hexanes) give isoxazolone 37.

The following compounds of Formula 4a identified in Table 7 are prepared analogously to Example 37.

TABLE 7

4a

| Example | R | Compound Name |
|---|---|---|
| 38 | (4-methylphenyl) | 4-(4-Fluorophenyl)-2-(4-methylphenyl)-3-pyridin-4-yl-2H-isoxazol-5-one |
| 39 | (4-methoxyphenyl) | 4-(4-Fluorophenyl)-2-(4-methoxyphenyl)-3-pyridin-4-yl-2H-isoxazol-5-one |
| 40 | (3,4-dimethoxyphenyl) | 2-(3,4-Dimethoxyphenyl)-4-(4-fluorophenyl)-3-pyridin-4-yl-2H-isoxazol-5-one |
| 41 | (2-methoxyphenyl) | 4-(4-Fluorophenyl)-2-(2-methoxyphenyl)-3-pyridin-4-yl-2H-isoxazol-5-one |
| 42 | (3-methoxyphenyl) | 4-(4-Fluorophenyl)-2-(3-methoxyphenyl)-3-pyridin-4-yl-2H-isoxazol-5-one |
| 43 | (benzo[1,3]dioxol-5-yl) | 2-(Benzo[1,3]dioxol-5-yl)-4-(4-fluorophenyl)-3-pyridin-4-yl-2H-isoxazol-5-one |

TABLE 7-continued

[Structure: 4-(4-fluorophenyl)-3-pyridin-4-yl-isoxazol-5(2H)-one with N-R substituent] (4a)

| Example | R | Compound Name |
|---|---|---|
| 44 | 4-phenoxyphenyl | 4-(4-Fluorophenyl)-2-(4-phenoxyphenyl)-3-pyridin-4-yl-2H-isoxazol-5-one |
| 45 | 4-(trifluoromethoxy)phenyl | 4-(4-Fluorophenyl)-3-pyridin-4-yl-2-(4-trifluoromethoxyphenyl)-2H-isoxazol-5-one |
| 46 | 4-(N,N-dimethylamino)phenyl | 2-[4-(N,N-Dimethylamino)-phenyl]-4-(4-fluorophenyl)-3-pyridin-4-yl-2H-isoxazol-5-one |
| 47 | 4-chlorophenyl | 2-(4-Chloro)-4-(4-fluorophenyl)-3-pyridin-4-yl-2H-isoxazol-5-one |
| 48 | 4-fluorophenyl | 2-(4-Fluoro)-4-(4-fluorophenyl)-3-pyridin-4-yl-2H-isoxazol-5-one |
| 49 | 4-(methylthio)phenyl | 4-(4-Fluorophenyl)-2-(4-methylthiophenyl)-3-pyridin-4-yl-2H-isoxazol-5-one |
| 50 | 4-(methylsulfonyl)phenyl | 4-(4-Fluorophenyl)-2-(4-methylsulfonyl-phenyl)-3-pyridin-4-yl-2H-isoxazol-5-one |
| 51 | 4-(methylsulfinyl)phenyl | 4-(4-Fluorophenyl)-2-(4-methylsulfinyl-phenyl)-3-pyridin-4-yl-2H-isoxazol-5-one |
| 52 | 4-(methoxycarbonyl)phenyl | 4-(4-Fluorophenyl)-2-(4-methoxycarbonyl-phenyl)-3-pyridin-4-yl-2H-isoxazol-5-one |

Example 53

2-(Ethoxymethyl)-4-(4-fluorophenyl)-3-(2-phenoxypyrimidin-4-yl)-2H-isoxazol-5-one a) 2-(4-Fluorophenyl)-3-hydroxy-3-(2-methylsulfanyl-pyrimidin-4-yl)-propionic acid methyl ester

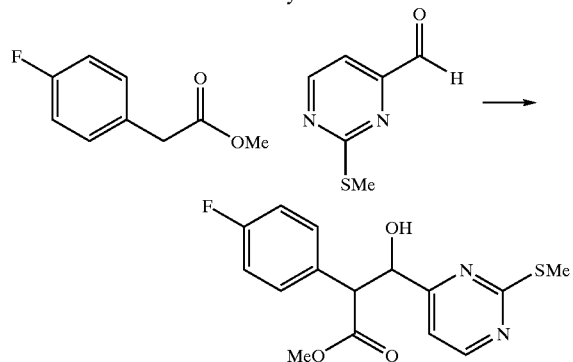

Using the procedure from Example 1a set forth above, substitute 2-methylsulfanyl-pyrimidine-4-carboxaldehyde for 4-pyridine carboxaldehyde to produce the title compound.

b) 2-(4-Fluorophenyl)-3-oxo-3-(2-methylsulfanyl-pyrimidin-4-yl)-propionic acid methyl ester

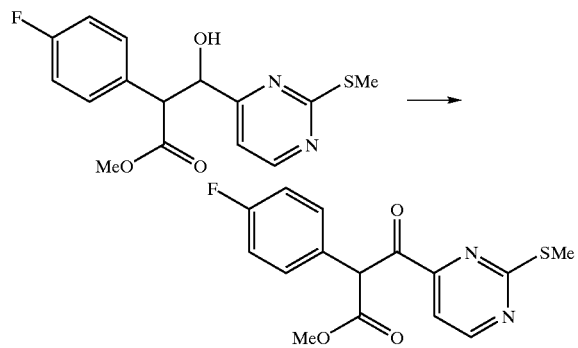

Using the procedure from Example 1b set forth above, substitute 2-(4-fluorophenyl)-3-hydroxy-3-(2-methylsulfanyl-pyrimidin-4-yl)-propionic acid methyl ester for 2-(4-fluorophenyl)-3-hydroxy-3-pyridin-4-yl-propionic acid methyl ester to produce the title compound.

c) 4-(4-Fluorophenyl)-3-(2-methylsulfanyl-pyrimidin-4-yl)-2H-isoxazol-5-one

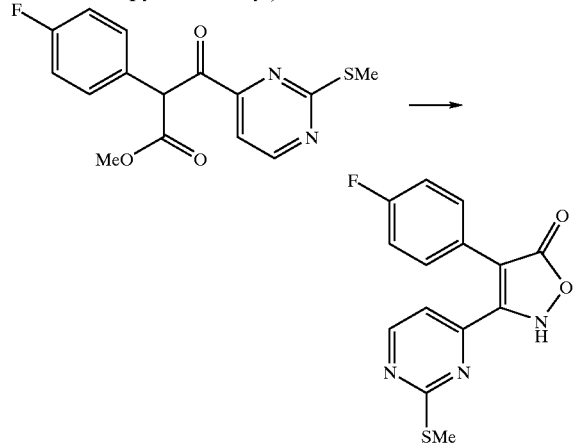

Using the procedure from Example 11 set forth above, substitute 2-(4-fluorophenyl)-3-oxo-3-(2-methylsulfanyl-pyrimidin-4-yl)-propionic acid methyl ester for 2-(4-fluorophenyl)-3-oxo-3-pyridin-4-yl-propionic acid methyl ester to produce the title compound.

d) 2-Ethoxymethyl-4-(4-fluorophenyl)-3-(2-methylsulfanyl-pyrimidin-4-yl)-2H-isoxazol-5-one

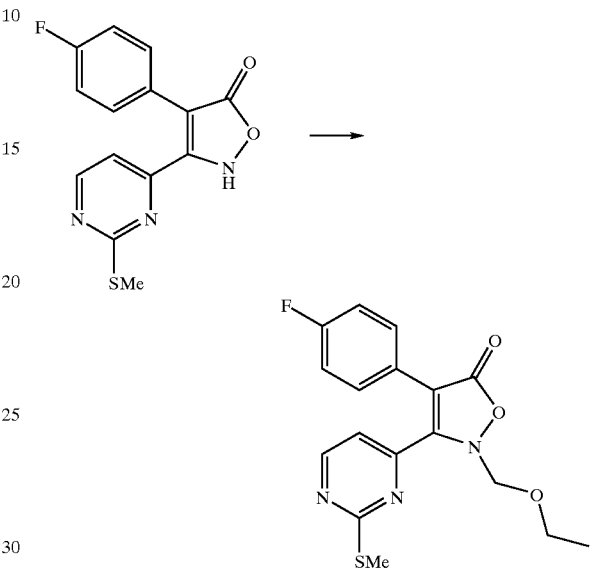

Using the procedure from Example 1m set forth above, substitute 4-(4-fluorophenyl)-3-(2-methylsulfanyl-pyrimidin-4-yl)-2H-isoxazol-5-one for 4-(4-fluorophenyl)-3-pyridin-4-yl-2H-isoxazol-5-one to produce the title compound. The following compounds of Formula 4b identified in Table 8 are prepared analogously to Example 53d.

TABLE 8

| Example | R | Compound Name |
|---|---|---|
| 54 | ~~~C(O)-N(piperazine)N-Me | 4-(4-Fluorophenyl)-2-(4-methylpiperazine-1-carbonyl)-3-(2-methylsulfanyl-pyrimidin-4-yl)-2H-isoxazol-5-one |
| 55 | ~~~C(O)-morpholine | 4-(4-Fluorophenyl)-2-(morpholine-4-carbonyl)-3-(2-methylsulfanyl-pyrimidin-4-yl)-2H-isoxazol-5-one |

TABLE 8-continued

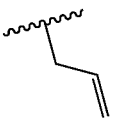

| Example | R | Compound Name |
|---|---|---|
| 56 | (allyl) | 2-Allyl-4-(4-fluorophenyl)-3-(2-methylsulfanyl-pyrimidin-4-yl)-2H-isoxazol-5-one | e) 2-Ethoxymethyl-4-(4-fluorophenyl)-3-(2-methylsulfonyl-pyrimidin-4-yl)-2H-isoxazol-5-one

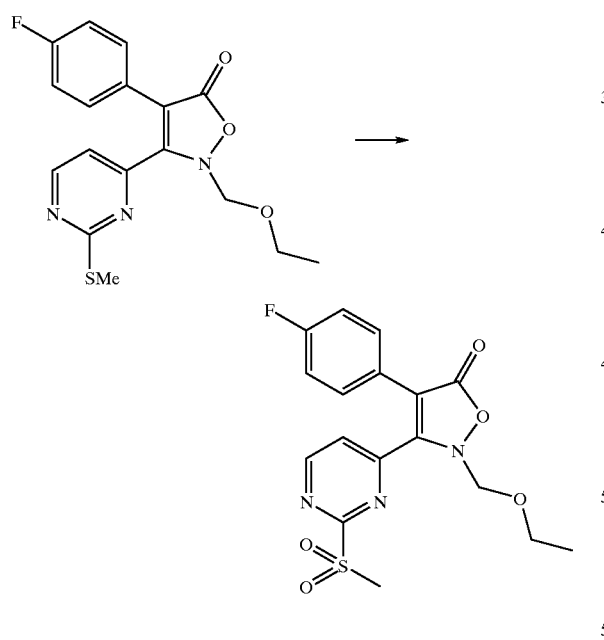

To a solution of isoxazolone 53d (0.50 g, 1.38 mmol) in THF:MeOH (24 mL of 1:1 mixture) is added a solution of Oxone® (0.61 g, 5.54 mmol) in H$_2$O (18 mL) dropwise. The reaction mixture is stirred for 1 h at room temperature, diluted with EtOAc and washed with aqueous NaHCO$_3$. The organic layer is dried over MgSO$_4$, filtered and concentrated under reduced pressure. The crude sulfone 53e is used without further purification.

f) 2-Ethoxymethyl-4-(4-fluorophenyl)-3-(2-phenoxy-pyrimidin-5-yl)-2H-isoxazol-5-one

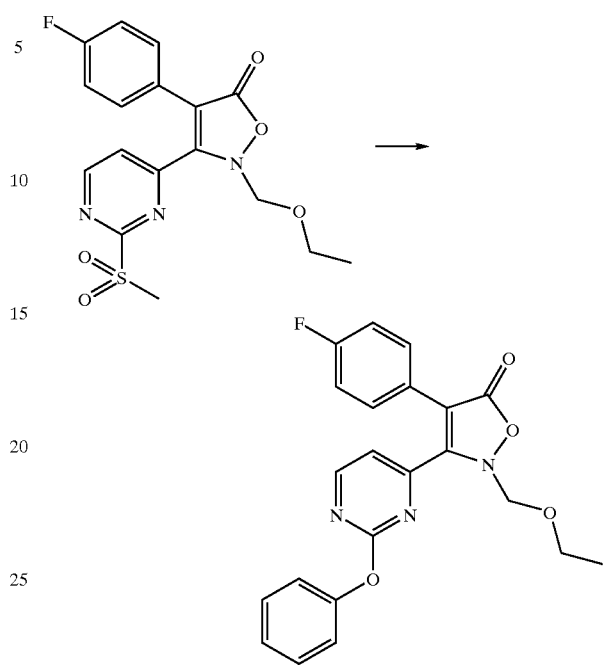

To a solution of phenol (0.14 g, 1.44 mmol) in THF (2 mL) is added NaH (0.05 g, 1.20 mmol) followed by a solution of crude sulfone 53e (0.17 g, 0.48 mmol) in THF (2 mL). The reaction mixture is stirred for 1 h at room temperature, diluted with EtOAc and washed with aqueous NaHCO$_3$ two times. The organic layer is dried over MgSO$_4$, filtered and concentrated under reduced pressure. Purification by flash chromatography (40% EtOAc: Hexanes) gives isoxazolone 53f as a yellow solid.

The following compounds of Formula 4c identified in Table 9 are prepared analogously to Example 53f.

TABLE 9

4c

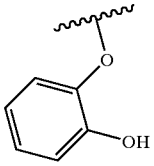

| Example | R | Compound Name |
|---|---|---|
| 57 | (2-hydroxyphenoxy) | 2-Ethoxymethyl-4-(4-fluorophenyl)-3-[2-(2-hydroxyphenoxy)-pyrimidin-4-yl]-isoxazol-5-one |

TABLE 9-continued

4c

| Example | R | Compound Name |
|---|---|---|
| 58 | (3-hydroxyphenoxy) | 2-Ethoxymethyl-4-(4-fluorophenyl)-3-[2-(3-hydroxyphenoxy)-pyrimidin-4-yl]-isoxazol-5-one |
| 59 | (2-acetamidophenoxy) | N-(2-{4-[2-Ethoxymethyl-4-(4-fluorophenyl)-5-oxo-2,5-dihydro-isoxazol-3-yl]-pyrimidin-2-yloxy}-phenyl)-acetamide |
| 60 | (2-methylamino-phenoxy) | 2-Ethoxymethyl-4-(4-fluorophenyl)-3-[2-(2-methylamino-phenoxy)-pyrimidin-4-yl]-2H-isoxazol-5-one |
| 61 | [(2-hydroxyphenyl)-methylamino] | 2-Ethoxymethyl-4-(4-fluorophenyl)-3-{2-[(2-hydroxyphenyl)-methylamino]-pyrimidin-4-yl}-2H-isoxazol-5-one |
| 62 | [(2-cyano)-methylamino] | 3-{2-[(2-cyano)-methylamino]-2-ethoxymethyl-4-(4-fluorophenyl)-pyrimidin-4-yl}-2H-isoxazol-5-one |

Example 63

(R)-2-Ethoxymethyl-4-(4-fluorophenyl)-3-[2-(1-phenyl-ethylamino)-pyrimidin-4-yl]-isoxazol-5-one

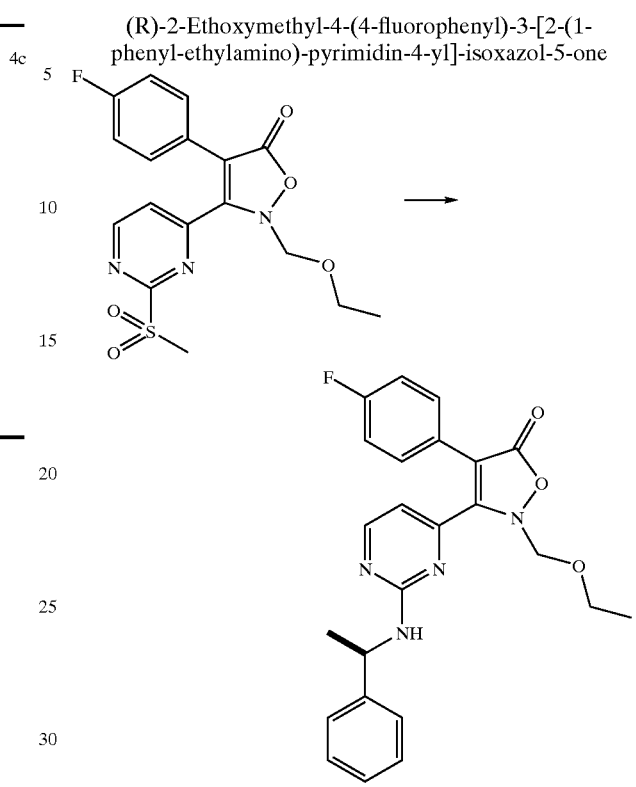

To a solution of isoxazolone 53e (0.15 g, 0.38 mmol) in toluene (2 mL) is added (R)-(+)-α-methylbenzylamine (2 mL). The reaction mixture is stirred for 2 h at 140° C. The excess amine and toluene were removed under reduced pressure. The resulting residue is diluted with EtOAc and washed with aqueous NaHCO$_3$. The organic layer is dried over MgSO$_4$, filtered and concentrated under reduced pressure. Purification by flash chromatography (50% EtOAc: Hexanes) gives isoxazolone 63 as a yellow solid.

The following compounds of Formula 4c identified in Table 10 are prepared analogously to Example 63.

TABLE 10

4c

| Example | R | Compound Name |
|---|---|---|
| 64 | benzylamino | 3-[2-(Benzylamino)-pyrimidin-4-yl]-2-ethoxymethyl-4-(4-fluoro-phenyl)-isoxazol-5-one |

TABLE 10-continued

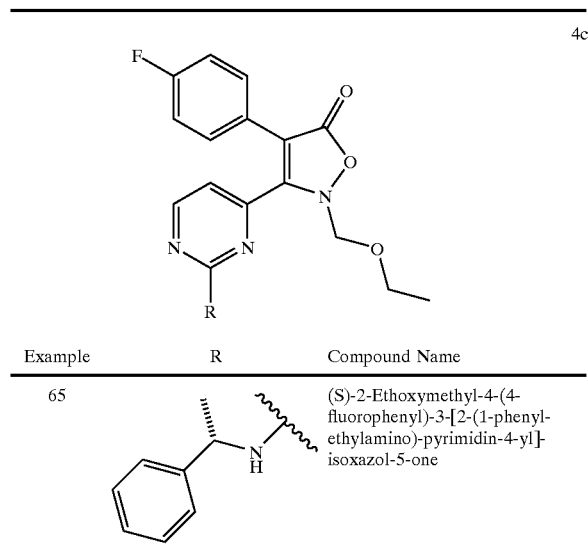

| Example | R | Compound Name |
|---|---|---|
| 65 | [(S)-1-phenylethylamino, NH] | (S)-2-Ethoxymethyl-4-(4-fluorophenyl)-3-[2-(1-phenyl-ethylamino)-pyrimidin-4-yl]-isoxazol-5-one |

Example 66

2-(N,N-Dimethylaminoethyl)-4-(4-fluorophenyl)-3-(2-phenoxy-pyrimidin-4-yl)-2H-isoxazol-5-one a) 2-Allyl-4-(4-fluorophenyl)-3-(2-methylsulfanyl-pyrimidin-4-yl)-2H-isoxazol-5-one

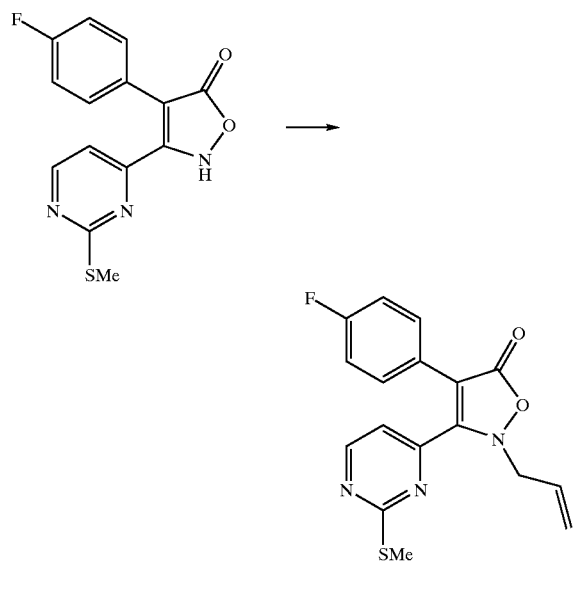

To a solution of 4-(4-fluorophenyl)-3-(2-thiomethylpyrimidin-4-yl)-2H-isoxazol-5-one (1.20 g, 3.96 mmol) in DMF (18 mL) is added sodium hydride (0.16 g, 3.96 mmol). After stirring for 10 min at room temperature, allyl bromide (0.53 mL, 5.94 mmol) is added dropwise. The reaction mixture is stirred at room temperature for 2.5 h, diluted with EtOAc and washed with aqueous saturated NH₄Cl. The organic layer is dried over MgSO₄ and filtered. The filtrate is concentrated under reduced pressure to give the crude product, which is purified by flash chromatography (40% EtOAc: Hexanes) to give isoxazolone 66.

b) 2-Allyl-4-(4-fluorophenyl)-3-(2-methanesulfonyl-pyrimidin-4-yl)-2H-isoxazol-5-one

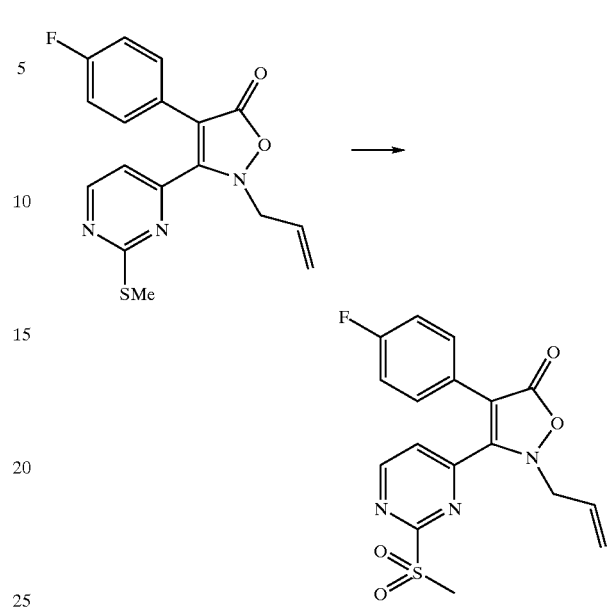

Using the procedure from Example 53e set forth above, substitute 2-allyl-4-(4-fluorophenyl)-3-(2-methylthiopyrimidin-4-yl)-2H-isoxazol-5-one for 2-ethoxymethyl-4-(4-fluorophenyl)-3-(2-methylthiopyrimidin-4-yl)-2H-isoxazol-5-one to produce the title compound.

c) 2-Allyl-4-(4-fluorophenyl)-3-(2-phenoxypyrimidin-5-yl)-2H-isoxazol-5-one

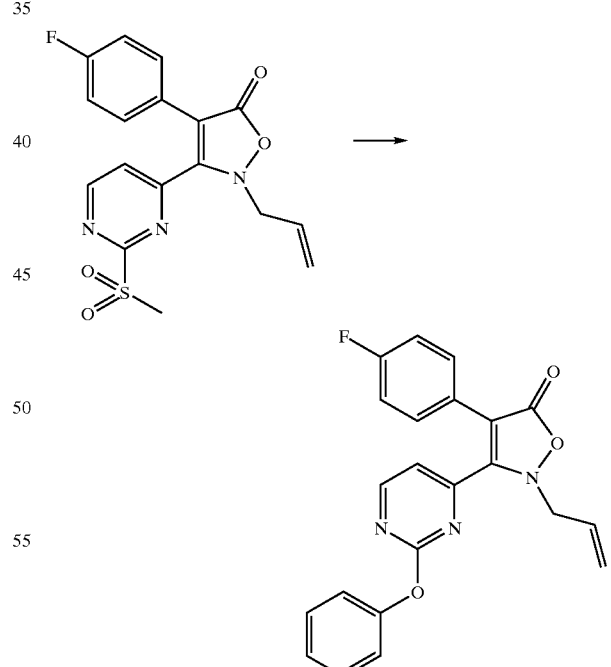

Using the procedure from Example 53f set forth above, substitute 2-allyl-4-(4-fluorophenyl)-3-(2-methylsulfonylpyrimidin-4-yl)-2H-isoxazol-5-one for 2-ethoxymethyl-4-(4-fluorophenyl)-3-(2-methylsulfonylpyrimidin-5-yl)-2H-isoxazol-5-one to produce the title compound.

d) [4-(4-Fluorophenyl)-5-oxo-3-(2-phenoxypyrimidin-4-yl)-5H-isoxazol-2-yl]-acetaldehyde

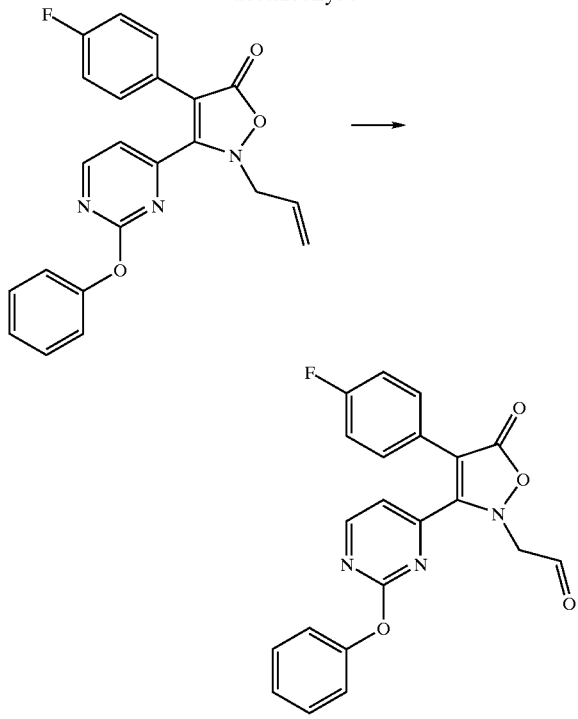

To a solution of isoxazolone 66c (0.19 g, 0.48 mmol), potassium ferricyanide (0.47 g, 1.44 mmol), K₂CO₃ (0.20 g, 1.44 mmol) and NaHCO₃ (0.12 g, 1.44 mmol) in tert-butanol (7 mL) is added H₂O (7 mL) followed by osmium tetraoxide (0.02 g, 0.08 mmol). After stirring for 15 h at room temperature, the reaction mixture is quenched with aqueous saturated NaHSO₃ and stirred for 10 min at room temperature. The solution is diluted with EtOAc and washed with H₂O. The organic layer is dried over MgSO₄, filtered and concentrated under reduced pressure.

To a solution of the resulting diol in THF:H₂O (6 mL of 1:1 mixture) is added sodium periodate (0.23 g, 1.07 mmol). The reaction mixture is stirred for 1.5 h at room temperature. The mixture is diluted with EtOAc and washed with aqueous saturated NaHCO₃. The organic layer is dried over MgSO₄ and filtered. The filtrate is concentrated under reduced pressure to give the crude product, which is purified by flash chromatography (60% EtOAc: Hexanes) to give aldehyde 66d.

e) 2-(N,N-Dimethylaminoethyl)-4-(4-fluorophenyl)-3-(2-phenoxy-pyrimidin-4-yl)-2H-isoxazol-5-one

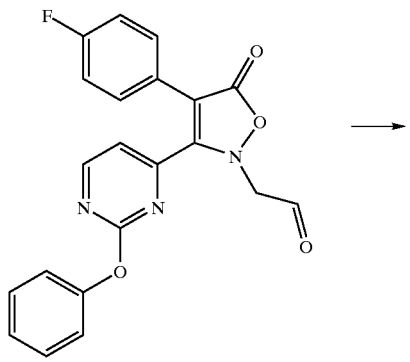

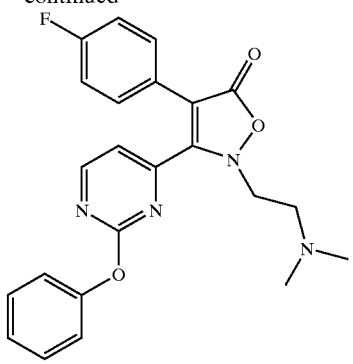

To a solution of aldehyde 66d (0.3 g, 0.76 mmol), dimethylamine (0.57 mL of a 2M solution in MeOH, 1.14 mmol), sodium acetate (0.25 g, 3.04 mmol) in MeOH (4 mL) is added sodium cyanoborohydride (0.07 g, 1.14 mmol). After stirring for 20 h at room temperature, the reaction mixture is filtered and the filtrate is concentrated under reduced pressure. The residue is diluted with aqueous saturated NH₄Cl and extracted with EtOAc. The organic layer is dried over MgSO₄, filtered and concentrated under reduced pressure. The crude residue is purified by flash chromatography (100% EtOAc) to give isoxazolone 66e.

The following compounds of Formula 4d identified in Table 11 are prepared analogously to Example 66d.

TABLE 11

4d

| Example | R₁—N—R₂ | Compound Name |
|---|---|---|
| 66 | ethyl, ethyl | 2-(N,N-Diethylaminoethyl)-4-(4-fluorophenyl)-3-(2-phenoxy-pyrimidin-4-yl)-2H-isoxazol-5-one |
| 67 | piperazinyl | 4-(4-Fluorophenyl)-2-(2-piperazin-1-ylethyl)-3-(2-phenoxy-pyrimidin-4-yl)-2H-isoxazol-5-one |

TABLE 11-continued

4d

| Example | R₁—N—R₂ | Compound Name |
|---|---|---|
| 68 | piperidinyl | 4-(4-Fluorophenyl)-2-(2-piperidin-1-ylethyl)-3-(2-phenoxy-pyrimidin-4-yl)-2H-isoxazol-5-one |
| 69 | morpholinyl | 4-(4-Fluorophenyl)-2-(2-morpholin-4-ylethyl)-3-(2-phenoxy-pyrimidin-4-yl)-2H-isoxazol-5-one |
| 70 | pyrrolidinyl | 4-(4-Fluorophenyl)-3-(2-phenoxy-pyrimidin-4-yl)2-(2-pyrrolidin-1-ylethyl)-2H-isoxazol-5-one |
| 71 | HN-CH₂CH₂-NH₂ | 2-[2-(2-Amino-ethylamino)ethyl]-4-(4-fluorophenyl)-3-(2-phenoxy-pyrimidin-4-yl)-2H-isoxazol-5-one |
| 72 | HN-CH₂CH₂-OH | 4-(4-Fluorophenyl)-2-[2-(2-hydroxy-ethylamino)ethyl]-3-(2-phenoxy-pyrimidin-4-yl)-2H-isoxazol-5-one |
| 73 | HN-CH₂CH₂-NMe₂ | [2-(2-Dimethylamino-ethylamino)-4-(4-fluorophenyl)-3-(2-phenoxy-pyrimidin-4-yl)-2H-isoxazol-5-one |
| 74 | HN-Et | (2-Ethylamino-ethyl)-4-(4-fluorophenyl)-3-(2-phenoxy-pyrimidin-4-yl)-2H-isoxazol-5-one |

Example 75

3-(4-fluorophenyl)-4-(2-thiomethylpyrimidin-4-yl)-2H-isoxazol-5-one a) 4-Fluoro-N-methoxy-N-methyl-benzamide

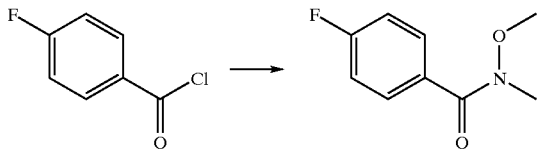

To a solution of commercially-available 4-fluorobenzoyl chloride (9.1 g, 57.4 mmol) and N,O-dimethylhydroxylamine (6.2 g, 63.1 mmol) in $CH_2Cl_2$ (200 mL) is added triethylamine (20.0 mL, 143.5 mmol) dropwise. After stirring 1.5 h at room temperature, the reaction mixture is diluted with EtOAc and washed with aqueous saturated $NaHCO_3$. The organic layer is dried over $MgSO_4$ and filtered. The filtrate is concentrated under reduced pressure to give the crude amide 75a, which is used without further purification.

b) 4-fluorophenyl-2-(2-thiomethylpyrimidin-4-yl)-ethanone

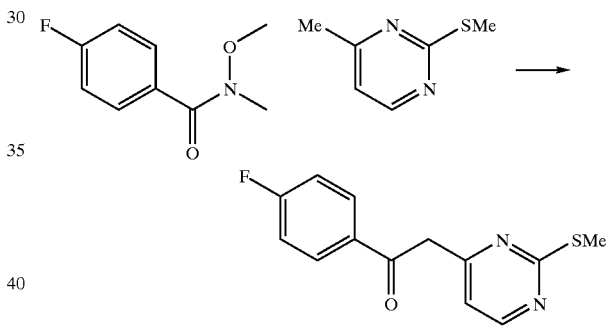

To a cold (−78° C.) solution of lithium diisopropylamide (27.0 mL of a 2M solution in THF, 54.0 mmol) in THF (60 mL) is added a solution of 4-methyl-2-thiomethylpyrimidine (5.0 g, 35.7 mmol) in THF (120 mL) dropwise. After stirring 15 min at −78° C., a solution of 4-fluoro-N-methoxy-N-methyl-benzamide (7.2 g, 39.3 mmol) in THF (30 mL) is added dropwise. The cold bath is replaced with a 0° C. ice bath and stirred for 2 h. The reaction mixture is quenched with $NH_4Cl$ and extracted with EtOAc. The organic layer is dried over $MgSO_4$ and filtered. The filtrate is concentrated under reduced pressure to give the crude ketone 75b, which is used without further purification.

c) 3-(4-Fluorophenyl)-3-oxo-2-(2-methylsulfanyl-pyrimidin-4-yl)-propionic acid ethyl ester

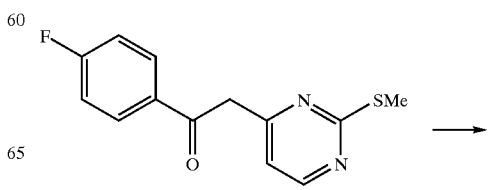

-continued

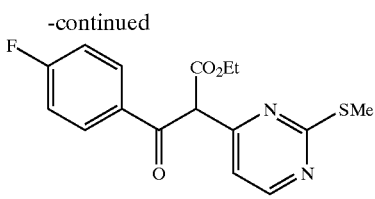

To a cold (0° C.) solution of potassium bis(trimethylsilyl) amide (36.6 mL of a 0.5M solution in toluene, 18.3 mmol) in THF (30 mL) is added a solution of 4-fluorophenyl-2-(2-thiomethylpyrimidin-4-yl)-ethanone (4.0 g, 15.3 mmol) in THF (30 mL) dropwise. After stirring 60 min at 0° C., ethyl chloroformate (1.6 mL, 16.8 mmol) is added dropwise. The reaction is slowly warmed to room temperature over 1.5 h. The reaction mixture is quenched with NH$_4$Cl and extracted with EtOAc. The organic layer is dried over MgSO$_4$, filtered and concentrated under reduced pressure. The crude residue is purified by flash chromatography (20% EtOAc/hexanes) to give ester 75c.

The following intermediates identified in Table 11 are prepared according to the method described immediately above substituting the appropriate starting materials.

TABLE 11

| Example | Structure |
|---|---|
| 75d | 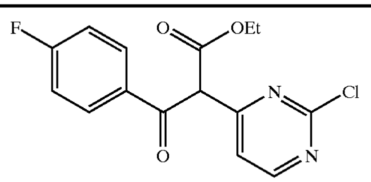 |
| 75e | 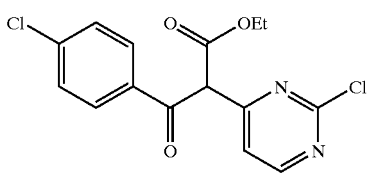 |
| 75f | 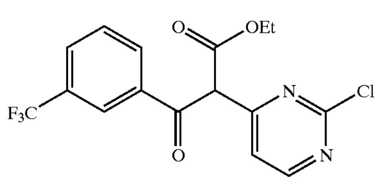 |
| 75g | 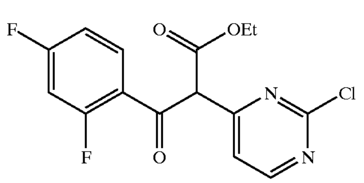 |
| 75h | 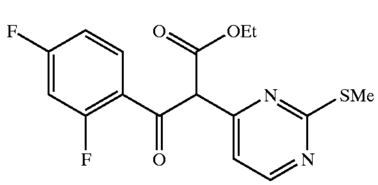 |

TABLE 11-continued

| Example | Structure |
|---|---|
| 75i | 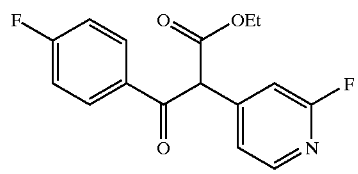 |
| 75j | 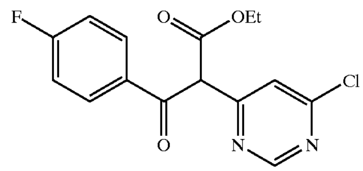 |
| 75k | | l) 3-(4-Fluorophenyl)-4-(2-methylsulfanyl-pyrimidin-4-yl)-2H-isoxazol-5-one

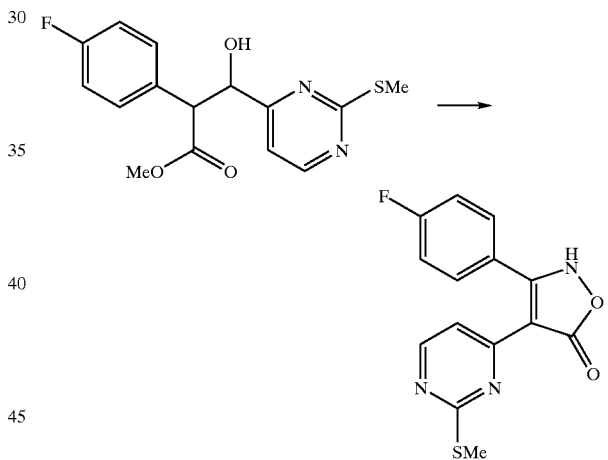

Using the procedure from Example 1k set forth above, substitute 3-(4-fluorophenyl)-3-oxo-2-(2-methylsulfanyl-pyrimidin-4-yl)-propionic acid ethyl ester for 2-(4-fluorophenyl)-3-oxo-3-pyridin-4-yl-propionic acid methyl ester and ethanol for pyridine to produce the title compound.

Methods of Use

As stated above, the compounds of the present invention are potent cytokine inhibitors. Accordingly, the compounds of Formula (I) or a pharmaceutically acceptable salt thereof can be used for the prophylactic or therapeutic treatment of diseases in humans or mammals that is associated with unwanted cytokine activity.

"Cytokine" as used herein refers to any secreted protein secreted by many different cell types involved in cell-to-cell communication and modulates interactions between cells in the inflammatory, immune or hematopoietic response. A cytokine includes, but is not limited to, monokines and lymphokines. Examples of cytokines include, but are not limited to, Interleukin-1 (IL-1), Tumor Necrosis Factor alpha and beta referred to collectively herein as (TNF), Interleukin-8 (IL-8) and Interleukin-6 (IL-6).

"Cytokine inhibition" as described herein, refers to: (i) a decrease of excessive in vivo levels of cytokines such as but not limited to IL-1, TNF, IL-6 and IL-8 to normal or sub-normal levels by inhibition of the in vivo release of the cytokines by all cells; (ii) a down regulation of the excessive expression of cytokine mRNA in vivo in a human to normal or sub-normal levels; (iii) a down regulation by inhibition of the direct synthesis of the cytokines such as but not limited to IL-1, TNF, IL-6 and IL-8 as a posttranslational event; or (iv) a down regulation, at the translational level, of excessive in vivo levels of cytokines such as but not limited to IL-1, TNF, IL-6 and IL-8 in a human to normal or sub-normal levels.

Compounds of Formula (I) are capable of inhibiting cytokines such as but not limited to IL-1, TNF, IL-6 and IL-8. These as well as other cytokines are important mediators of inflammation in a wide variety of diseases. The inhibition of these inflammatory cytokines is of benefit in treating many of these disease states. The invention also provides a method of treating a proteinase mediated disease in humans or mammals, wherein the production of the proteinase is affected by cytokines. Examples of such proteinases include but are not limited to the matrix metalloproteinases and disintegrin metalloproteases (ADAMs).

The ability of compounds of Formula (I) to inhibit TNF-α production is measured using lipopolysaccharide (LPS) stimulated human monocytic cells (THP-1) (See: (a) Mohler K. M., et al. "Protection against a lethal dose of endotoxin by an inhibitor of tumour necrosis factor processing" *Nature* 1994, 370, 218–220; (b) Regan J. R., et al. "Aromatic heterocyclic compounds as anti-inflammatory agents" WO 99/23091, PCT/US98/22907). Test compounds are incubated at various concentrations with THP-1 cells for 15 minutes before the stimulation of cytokine release by the addition of LPS (2

The compounds of Formula (I) are administered in a amount sufficient to inhibit cytokines such as but not limited to IL-1, TNF, IL-6 and IL-8, so that it is regulated to normal or subnormal levels, so as to prevent the disease state. The amount of cytokine considered abnormal for the present invention, constitute; levels of free cytokines such as but not limited to IL-1, TNF, IL-6 and IL-8 greater than or equal to 1 picogram per ml; any cell associated cytokines or; the presence of cytokine mRNA above basal levels in cells or tissues.

Therefore, these compounds are useful therapeutic agents for the treatment of diseases associated with unwanted cytokine activity including, osteoarthritis, rheumatoid arthritis, septic arthritis, psoriatic arthritis, rheumatic fever, gout, Reiter's syndrome, osteoperosis, diabetes, inflammatory bowel diseases including Crohn's disease and ulcerative colitis, pancreatitis, diverticulitis, sepsis, septic shock, toxic shock syndrome, respiratory diseases including asthma, chronic obstructive pulmonary disease (COPD), bronchitis, emphysema, cystic fibrosis, acute respiratory distress, fibrotic diseases of the lung and liver, diseases of the central nervous system such as Alzheimer's disease, amyotrophic lateral sclerosis (ALS), muscular dystrophy and multiple sclerosis, HIV/AIDS, cachexia secondary to infection or malignancy and cachexia secondary to acquired immune deficiency syndrome.

Since cytokines can cause the overproduction of proteinases, the compounds of this invention are useful in preventing prosthesis loosening. It is known in the art that over time prostheses loosen, become painful, and may result in further bone injury, thus requiring replacement. The need for replacement of such prostheses includes those such as in, joint replacements (for example hip, knee and shoulder replacements), dental prosthesis, including dentures, bridges and prosthesis secured to the maxilla and/mandible.

Cytokines and proteinases are also active in remodeling in the cardiovascular system. It has been suggested that one of the reasons angioplasty has a higher than expected long term failure rate (reclosure over time) is that cytokine and proteinase activity is not desired or is elevated in response to what may be recognized by the body as "injury" to the basement membrane of the vessel. Similarly restenosis of surgical cardiovascular stents is thought to be mediated by cytokine induced proteinase production in response to "injury" induced by placement of the stent.

Compounds of this invention are also useful for the treatment of diseases which are caused by excessive or inappropriate angiogenesis. Such diseases, conditions or disorders include but are not limited to, various ocular diseases, such as macular degeneration and diabetic retinopathy, tumor growth and metastasis, atherosclerosis and rheumatoid arthritis.

In skin care, cytokines are implicated in the remodeling or 'turnover' of skin. As a result, the regulation of cytokines improves treatment of skin conditions including but not limited to, wrinkle repair, regulation, prevention and repair of ultraviolet induced skin damage. Such a treatment includes prophylactic treatment or treatment before the physiological manifestations are obvious. For example, the cytokine inhibitor may be applied as a preexposure treatment to prevent ultraviolet damage and/or during or after exposure to prevent or minimize post-exposure damage. In addition, cytokines are implicated in skin disorders and diseases related to abnormal tissues that result from abnormal turnover such as epidermolysis bullosa, psoriasis, scleroderma and atopic dermatitis. The compounds of this invention are also useful for treating the consequences of "normal" injury to the skin including scarring or "contraction" of tissue for example, following burns and perhaps the regulation of hair growth.

Inhibition of cytokines are also thought to be useful for the treatment of ocular disorders (especially corneal ulceration, lack of corneal healing, macular degeneration and pterygium) gum disease (especially periodontal disease and gingivitis). Compounds preferred for, but not limited to, the treatment of ocular disorders, gum disease, and skin diseases may be administered topically.

Compositions

The compositions of the invention comprise:

(a) a safe and effective amount of a compound of the invention; and (b) a pharmaceutically-acceptable carrier.

As discussed above, numerous diseases are known to be mediated by excess or undesired cytokine activity. For example, these include osteoarthritis, rheumatoid arthritis, diabetes, HIV/AIDS, inflammatory bowel disease, chronic heart failure, hypertension, periodontitis and the like. Thus, the compounds of the invention are useful in the treatment or prevention of conditions involving this unwanted activity.

The invention compounds can therefore be formulated into pharmaceutical compositions for use in treatment or prophylaxis of these conditions. Standard pharmaceutical formulation techniques are used, such as those disclosed in *Remington's Pharmaceutical Sciences*, Mack Publishing Company, Easton, Pa., latest edition.

A "safe and effective amount" of a Formula (I) compound is an amount that is effective, to inhibit cytokines at the site(s) of activity, in an animal, preferably a mammal, more preferably a human subject, without undue adverse side effects (such as toxicity, irritation, or allergic response), commensurate with a reasonable benefit/risk ratio when used in the manner of this invention. The specific "safe and effective amount" will, obviously, vary with such factors as the particular condition being treated, the physical condition of the patient, the duration of treatment, the nature of concurrent therapy (if any), the specific dosage form to be used, the carrier employed, the solubility of the Formula (I) compound therein, and the dosage regimen desired for the composition.

In addition to the subject compound, the compositions of the subject invention contain a pharmaceutically-acceptable carrier. The term "pharmaceutically-acceptable carrier", as used herein, means one or more compatible solid or liquid filler diluents or encapsulating substances which are suitable for administration to an animal, preferably a mammal, more preferably a human. The term "compatible", as used herein, means that the components of the composition are capable of being commingled with the subject compound, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the animal, preferably a mammal, more preferably a human being treated.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the Tweens®; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

If the subject compound is to be injected, the preferred pharmaceutically-acceptable carrier is sterile, physiological saline, with blood-compatible suspending agent, the pH of which has been adjusted to about 7.4.

In particular, pharmaceutically-acceptable carriers for systemic administration include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Preferred carriers for parenteral administration include propylene glycol, ethyl oleate, pyrrolidone, ethanol, and sesame oil. Preferably, the pharmaceutically-acceptable carrier, in compositions for parenteral administration, comprises at least about 60%, more preferably at least about 90%, by weight of the total composition.

The compositions of this invention are preferably provided in unit dosage form. As used herein, a "unit dosage form" is a composition of this invention containing an amount of a Formula (I) compound that is suitable for administration to an animal, preferably a mammal, more preferably a human subject, in a single dose, according to good medical practice. These compositions preferably contain from about 5 mg (milligrams) to about 1000 mg, more preferably from about 10 mg to about 500 mg, more preferably from about 10 mg to about 300 mg, of a Formula (I) compound.

The compositions of this invention may be in any of a variety of forms, suitable (for example) for oral, rectal, topical, nasal, ocular or parenteral administration. Depending upon the particular route of administration desired, a variety of pharmaceutically-acceptable carriers well-known in the art may be used. These include solid or liquid fillers, diluents, hydrotropes, surface-active agents, and encapsulating substances. Optional pharmaceutically-active materials may be included, which do not substantially interfere with the inhibitory activity of the Formula (I) compound. The amount of carrier employed in conjunction with the Formula (I) compound is sufficient to provide a practical quantity of material for administration per unit dose of the Formula (I) compound. Techniques and compositions for making dosage forms useful in the methods of this invention are described in the following references, all incorporated by reference herein: *Modern Pharmaceutics*, Chapters 9 and 10 (Banker & Rhodes, editors, 1979); Lieberman et al., *Pharmaceutical Dosage Forms: Tablets* (1981); and Ansel, *Introduction to Pharmaceutical Dosage Forms* 2d Edition (1976).

Various oral dosage forms can be used, including such solid forms as tablets, capsules, granules and bulk powders. These oral forms comprise a safe and effective amount, usually at least about 5%, and preferably from about 25% to about 50%, of the Formula (I) compound. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carrier suitable for the preparation of unit dosage forms for peroral administration are well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical for the purposes of the subject invention, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, Avicel RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions of the subject invention may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

The compositions of this invention can also be administered topically to a subject, e.g., by the direct laying on or spreading of the composition on the epidermal or epithelial tissue of the subject, or transdermally via a "patch". Such compositions include, for example, lotions, creams, solutions, gels and solids. These topical compositions preferably comprise a safe and effective amount, usually at least about 0.1%, and preferably from about 1% to about 5%, of the Formula (I) compound. Suitable carriers for topical administration preferably remain in place on the skin as a continuous film, and resist being removed by perspiration or immersion in water. Generally, the carrier is organic in nature and capable of having dispersed or dissolved therein the Formula (I) compound. The carrier may include pharmaceutically-acceptable emollients, emulsifiers, thickening agents, solvents and the like.

Modes of Administration

This invention also provides methods of treating or preventing disorders associated with excess or undesired cytokine activity in a human or other animal subject, by administering a safe and effective amount of a Formula (I) compound to said subject. The methods of the invention are useful in treating or preventing disorders described above.

Compositions of this invention can be administered topically or systemically. Systemic application includes any method of introducing Formula (I) compound into the tissues of the body, e.g., intra-articular (especially in treatment of rheumatoid arthritis), intrathecal, epidural, intramuscular, transdermal, intravenous, intraperitoneal, subcutaneous, sublingual, rectal, and oral administration. The Formula (I) compounds of the present invention are preferably administered orally.

The specific dosage of inhibitor to be administered, as well as the duration of treatment, and whether the treatment is topical or systemic are interdependent. The dosage and treatment regimen will also depend upon such factors as the specific Formula (I) compound used, the treatment indication, the ability of the Formula (I) compound to reach minimum inhibitory concentrations at the site of the metalloprotease to be inhibited, the personal attributes of the subject (such as weight), compliance with the treatment regimen, and the presence and severity of any side effects of the treatment.

Typically, for a human adult (weighing approximately 70 kilograms), from about 5 mg to about 3000 mg, more preferably from about 5 mg to about 1000 mg, more preferably from about 10 mg to about 100 mg, of Formula (I) compound are administered per day for systemic administration. It is understood that these dosage ranges are by way of example only, and that daily administration can be adjusted depending on the factors listed above.

A preferred method of administration for treatment of rheumatoid arthritis is oral or parenterally via intra-articular injection. As is known and practiced in the art, all formulations for parenteral administration must be sterile. For mammals, especially humans, (assuming an approximate body weight of 70 kilograms) individual doses of from about 10 mg to about 1000 mg are preferred.

A preferred method of systemic administration is oral. Individual doses of from about 10 mg to about 1000 mg, preferably from about 10 mg to about 300 mg are preferred.

Topical administration can be used to deliver the Formula (I) compound systemically, or to treat a subject locally. The amounts of Formula (I) compound to be topically administered depends upon such factors as skin sensitivity, type and location of the tissue to be treated, the composition and carrier (if any) to be administered, the particular Formula (I) compound to be administered, as well as the particular disorder to be treated and the extent to which systemic (as distinguished from local) effects are desired.

The inhibitors of the invention can be targeted to specific locations where the cytokine is accumulated by using targeting ligands. For example, to focus the inhibitors to cytokine contained in a specific cell type, the inhibitor is conjugated to an antibody or fragment thereof which is immunoreactive with a cellular marker as is generally understood in the preparation of immunotoxins in general. The targeting ligand can also be a ligand suitable for a receptor which is present on the target cell. Any targeting ligand which specifically reacts with a marker for the intended target tissue can be used. Methods for coupling the invention compound to the targeting ligand are well known and are similar to those described below for coupling to carrier. The conjugates are formulated and administered as described above.

For localized conditions, topical administration is preferred. For example, to treat ulcerated cornea, direct application to the affected eye may employ a formulation as eyedrops or aerosol. For corneal treatment, the compounds of the invention can also be formulated as gels, drops or ointments, or can be incorporated into collagen or a hydrophilic polymer shield. The materials can also be inserted as a contact lens or reservoir or as a subconjunctival formulation. For treatment of skin inflammation, the compound is applied locally and topically, in a gel, paste, salve or ointment. For treatment of oral diseases, the compound may be applied locally in a gel, paste, mouth wash, or implant. The mode of treatment thus reflects the nature of the condition and suitable formulations for any selected route are available in the art.

In all of the foregoing, of course, the compounds of the invention can be administered alone or as mixtures, and the compositions may further include additional drugs or excipients as appropriate for the indication.

All documents cited in the Detailed Description of the Invention are, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A compound having a structure according to Formula (I):

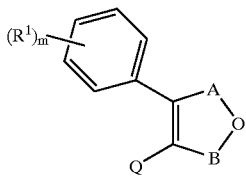

wherein:
a. each $R^1$ is selected from the group consisting of lower alkyl, CN, and halo;
b. m is an integer 1 or 2;

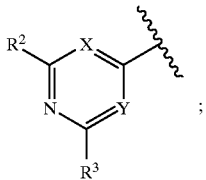

c. Q is
d. $R^2$ is H;
e. $R^3$ is selected from the group consisting of: H, alkyl, OH, $OR^4$, and $SR^4$;
f. X is CH;
g. Y is N;
h. A is selected from the group consisting of: C(O) and N-G;
i. B is selected from the group consisting of: C(O) and N-G;
j. Provided that one and only one of A or B is C(O);
k. G is selected from the group consisting of: alkyl, cycloalkyl, aryl, heteroalkyl, heterocycloalkyl, heteroaryl, $OR^4$ and $S(O)_2R^4$;
l. each $R^4$ is independently selected from H, lower alkyl, lower alkenyl, lower alkynyl, cycloalkyl, cycloalkenyl, aryl, heteroalkyl, heteroalkenyl, heteroalkynyl, heterocycloalkyl, heterocycloalkenyl, and heteroaryl;
m. each $R^5$ is independently selected from H, lower alkyl, lower alkenyl, lower alkynyl, cycloalkyl, cycloalkenyl, aryl, heteroalkyl, heteroalkenyl, heteroalkynyl, heterocycloalkyl, heterocycloalkenyl, heteroaryl, $OR^4$, and $S(O)_2R^4$;
or an optical isomer, diastereomer or enantiomer for Formula (I), or a pharmaceutically-acceptable salt thereof.

2. The compound according to claim 1 wherein G is selected from the group consisting of: alkyl, aryl, heteroalkyl, and heterocycloalkyl.

3. The compound according to claim 1 wherein $R^4$ is selected from the group consisting of: phenyl, lower alkyl, and heteroaryl.

4. The compound according to claim 3 herein each $R^1$ is independently selected from the group consisting of: F, Cl, $CF_3$, CN, and $CH_3$.

5. The compound according to claim 4 herein A is C(O).

6. The compound according to claim 4 herein B is C(O).

7. A compound selected from the group consisting of:

4-(4-Fluorophenyl)-3-(2-methylsulfanyl-pyrimidin-4-yl)-2H-isoxazol-5-one;

2-Ethoxymethyl-4-(4-fluorophenyl)-3-(2-methylsulfanyl-pyrimidin-4-yl)-2H-isoxazol-5-one;

4-(4-Fluorophenyl)-2-(4-methylpiperazine-1-carbonyl)-3-(2-methylsulfanyl-pyrimidin-4-yl)-2H-isoxazol-5-one;

4-(4-Fluorophenyl)-2-(morpholine-4-carbonyl)-3-(2-methylsulfanyl-pyrimidin-4-yl)-2H-isoxazol-5-one;

2-Allyl-4-(4-fluorophenyl)-3-(2-methylsulfanyl-pyrimidin-4-yl)-2H-isoxazol-5-one;

2-Ethoxymethyl-4-(4-fluorophenyl)-3-[2-(2-hydroxyphenoxy)-pyrimidin-4-yl]-isoxazol-5-one;

2-Ethoxymethyl-4-(4-fluorophenyl)-3-[2-(3-hydroxyphenoxy)-pyrimidin-4-yl]-isoxazol-5-one;

2-Ethoxymethyl-4-(4-fluorophenyl)-3-(2-phenoxy-pyrimidin-5-yl)-2H-isoxazol-5-one;

3-{2-[(2-cyano)-methylamino]-2-ethoxymethyl-4-(4-fluorophenyl)-pyrimidin-4-yl}-2H-isoxazol-5-one;

3-[2-(Benzylamino)-pyrimidin-4-yl]-2-ethoxymethyl-4-(4-fluorophenyl)-isoxazol-5-one;

(R)-2-Ethoxymethyl-4-(4-fluorophenyl)-3-[2-(1-phenyl-ethylamino)-pyrimidin-4-yl]-isoxazol-5-one;

(S)-2-Ethoxymethyl-4-(4-fluorophenyl)-3-[2-(1-phenyl-ethylamino)-pyrimidin-4-yl]-isoxazol-5-one;

N-(2-{4-[2-Ethoxymethyl-4-(4-fluorophenyl)-5-oxo-2,5-dihydro-isoxazol-3-yl]-pyrimidin-2-yloxy}-phenyl)-acetamide;

2-Ethoxymethyl-4-(4-fluorophenyl)-3-[2-(2-methylamino-phenoxy)-pyrimidin-4-yl]-2H-isoxazol-5-one;

2-Ethoxymethyl-4-(4-fluorophenyl)-3-{2-[(2-hydroxyphenyl)-methylamino]-pyrimidin-4-yl}-2H-isoxazol-5-one;

2-Allyl-4-(4-fluorophenyl)-3-(2-methylsulfanyl-pyrimidin-4-yl)-2H-isoxazol-5-one;

2-Allyl-4-(4-fluorophenyl)-3-(2-phenoxypyrimidin-5-yl)-2H-isoxazol-5-one;

[4-(4-Fluorophenyl)-5-oxo-3-(2-phenoxypyrimidin-4-yl)-5H-isoxazol-2-yl]-acetaldehyde;

2-(N,N-Dimethylaminoethyl)-4-(4-fluorophenyl)-3-(2-phenoxy-pyrimidin-4-yl)-2H-isoxazol-5-one;

2-(N,N-Diethylaminoethyl)-4-(4-fluorophenyl)-3-(2-phenoxy-pyrimidin-4-yl)-2H-isoxazol-5-one;

4-(4-Fluorophenyl)-2-(2-piperazin-1-ylethyl)-3-(2-phenoxy-pyrimidin-4-yl)-2H-isoxazol-5-one;

4-(4-Fluorophenyl)-2-(2-piperidin-1-ylethyl)-3-(2-phenoxy-pyrimidin-4-yl)-2H-isoxazol-5-one;

4-(4-Fluorophenyl)-2-(2-morpholin-4-ylethyl)-3-(2-phenoxy-pyrimidin-4-yl)-2H-isoxazol-5-one;

4-(4-Fluorophenyl)-3-(2-phenoxy-pyrimidin-4-yl)2-(2-pyrrolidin-1-ylethyl)-2H-isoxazol-5-one;

2-[2-(2-Amino-ethylamino)ethyl]-4-(4-fluorophenyl)-3-(2-phenoxy-pyrimidin-4-yl)-2H-isoxazol-5-one;

4-(4-Fluorophenyl)-2-[2-(2-hydroxy-ethylamino)ethyl]-3-(2-phenoxy-pyrimidin-4-yl)-2H-isoxazol-5-one;

[2-(2-Dimethylamino-ethylamino)-4-(4-fluorophenyl)-3-(2-phenoxy-pyrimidin-4-yl)-2H-isoxazol-5-one;

(2-Ethylamino-ethyl)-4-(4-fluorophenyl)-3-(2-phenoxy-pyrimidin-4-yl)-2H-isoxazol-5-one; and 3-(4-Fluorophenyl)-4-(2-methylsulfanyl-pyrimidin-4-yl)-2H-isoxazol-5-one.

8. A pharmaceutical composition comprising:

(a) a safe and effective amount of a compound of claim 1; and (b) a pharmaceutically-acceptable carrier.

9. A method for treating osteoarthritis, the method comprising administering to said subject a safe and effective amount of a compound of claim 1.

10. A method for treating rheumatoid arthritis, the method comprising administering to said subject a safe and effective amount of a compound of claim 1.

11. A method for treating congestive heart failure, the method comprising administering to said subject a safe and effective amount of a compound of claim 1.

* * * * *